US008758741B2

(12) United States Patent
Takagi et al.

(10) Patent No.: US 8,758,741 B2
(45) Date of Patent: Jun. 24, 2014

(54) GENE EXPRESSION CASSETTE AND A TRANSFORMANT, AND A METHOD FOR MANUFACTURING 2-DEOXY-SCYLLO-INOSOSE AND A METHOD FOR PURIFYING 2-DEOXY-SCYLLO-INOSOSE USING SAID TRANSFORMANT

(75) Inventors: Masamichi Takagi, Fuchu (JP); Takahisa Kogure, Kashiwa (JP); Naoki Wakisaka, Niigata (JP); Hiroaki Takaku, Niigata (JP); Katsumi Ajisaka, Niigata (JP); Tatsuo Miyazaki, Niigata (JP); Masao Hirayama, Niigata (JP)

(73) Assignees: Mitsui Chemicals, Inc., Tokyo (JP); Niigata Bio-Research Park, Inc., Tokyo (JP)

( * ) Notice: Subject to any disclaimer, the term of this patent is extended or adjusted under 35 U.S.C. 154(b) by 994 days.

(21) Appl. No.: 11/887,445

(22) PCT Filed: Mar. 23, 2006

(86) PCT No.: PCT/JP2006/305782
§ 371 (c)(1),
(2), (4) Date: Sep. 28, 2007

(87) PCT Pub. No.: WO2006/109479
PCT Pub. Date: Oct. 19, 2006

(65) Prior Publication Data
US 2010/0015672 A1 Jan. 21, 2010

(30) Foreign Application Priority Data
Mar. 30, 2005 (WO) .................. PCT/JP2005/006022

(51) Int. Cl.
*A01N 63/00* (2006.01)
*C12N 15/09* (2006.01)
*C12N 15/63* (2006.01)
*C07H 21/04* (2006.01)

(52) U.S. Cl.
USPC ........ 424/93.2; 435/320.1; 435/455; 536/23.2

(58) Field of Classification Search
USPC ............... 424/93.2; 435/320.1, 455; 536/23.2
See application file for complete search history.

(56) References Cited

FOREIGN PATENT DOCUMENTS

JP 2000-236881 A 9/2000
JP 2005-000072 A 1/2005

OTHER PUBLICATIONS

Kudo et al., 1999, The Journal of Antibiotics, vol. 52, No. 6, p. 559-571.*
Houriyou et al., 1997, JP 09327297, search result, including abstract.*
Fraenkel, D.G., 1968, The Journal of Biological Chemistry, vol. 243, No. 24, pp. 6451-6457.*
Houdebine, L-M., 2002, Journal of Biotechnology, vol. 98, p. 145-160.*
Mercier et al., 1997, "The modification of milk protein composition through transgenesis: progress and problems," In: Transgenic Animals: Generation and use, Ed. Houdebine LM, Harwood Academic Publishers, The Netherlands pp: 473-482.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Rescher et al., 2004, Journal of Cell Science, vol. 117, p. 2631-2639.*
Schalkwyk et al., 2007, Genes, Brain and Behavior, vol. 6, p. 299-303.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Kodama et al., 2006, Current Medicinal Chemistry, vol. 13, p. 2155-2161.*
Fumitaka Kudo et al., "Molecular Cloning of the Gene for the Key Carbocycle-forming Enzyme in the biosynthesis of 2-Deoxystreptamine-containing Aminocyclitol Antibiotics and its Comparison with Dehydroquinate Synthase", The Journal of Antibiotics, Jun. 1999, pp. 559-571, vol. 52, No. 6.
Noriaki Yamauchi et al., "Biochemical Studies on 2-Deoxy-scyllo-inosose, an Early Intermediate in the Biosynthesis of 2-Deoxystreptamine", The Journal of Antibiotics, May 1992, pp. 756-766, vol. 45, No. 5.
Gao et al., *Kinetic measurements of phosphoglucose isomerase and phosphomannose isomerase by direct analysis of phosphorylated aldose-ketose isomers using tandem mass spectrometry*, 240 Science 291-299 (2005).
Kudo et al., Purification and Characterization of 2-Dexoy-scyllo-inosose Synthase Derived from *Bacillus circulans. A crucial Carbocyclization Enzyme in the Biosynthesis of 2-Deoxystreptamine-containing Aminoglycoside Antibiotics*, 52(2) The Journal of Antibiotics 81-88 (1999).
Morita et al., *Accumulation of glucose 6-Phosphate or Fructose 6-Phosphate Is Responsible for Destabilization of Glucose Transporter mRNA in Escherichia coli*, 278(18) The Journal of Biological Chemistry 15608-15614 (2003).
Roman et al., *Overexpression of UDP-glucose dehydrogenase in Escherichia coli results in decreased biosynthesis of K5 polysaccharide*, 374 Biochem J. 767-772 (2003).
Yokoyama et al., *Production of New Carotenoids, Astaxanthin Glucosides, by Escherichia coli Transformants Carrying Carotenoid Biosynthetic Genes*, 39 Tetrahedron Letters 3709-3712 (1998).

* cited by examiner

*Primary Examiner* — Shin-Lin Chen
(74) *Attorney, Agent, or Firm* — Buchanan Ingersoll & Rooney PC

(57) ABSTRACT

A transformant is prepared to insert at least a gene expression cassette comprising a gene involved in the synthesis of 2-deoxy-scyllo-inosose into *E. coli* as host cells. A 2-deoxy-scyllo-inosose is synthesized from D-glucose, oligosaccharide, polysaccharide, starch and rice bran, using the transformant. A culture solution containing the 2-deoxy-scyllo-inosose is treated with a mixed bed or double bed type column comprising a hydrogen form of strong acidic cation exchange resin and an organic ion form of basic anion exchange resin. The 2-deoxy-scyllo-inosose as purified is reacted with trimethoxymethane to convert into 2-deoxy-scyllo-inosose dimethylketal, and the dimethylketal is crystallized and purified. Then, DOI is highly purified through hydrolyzing the dimethylketal in the presence of acid.

1 Claim, 22 Drawing Sheets

Plasmid name: pGAP-btrC
Plasmid size: 4.30 kb
Constructed by:
Construction date:
Comment&Reference:

Plasmid name: pGAD-btrC
Plasmid size: 3.93 kb
Constructed by:
Construction date:
Comment&Reference:

Plasmid name: pGAP-btrC/pGAD-btrC
Plasmid size: 5.67 kb
Constructed by:
Construction date:
Comment&Reference:

SEQUENCE LISTING

```
<160> NUMBER OF SEQ ID NOS: 22

<210> SEQ ID NO 1
<211> LENGTH: 31
<212> TYPE: DNA
<213> ORGANISM: artificial sequence
<220> FEATURE:
<223> OTHER INFORMATION: primer1

<400> SEQUENCE: 1
gggaattcca tatgacgact aaacaaattt g                                  31

<210> SEQ ID NO 2
<211> LENGTH: 29
<212> TYPE: DNA
<213> ORGANISM: artificial sequence
<220> FEATURE:
<223> OTHER INFORMATION: primer 2

<400> SEQUENCE: 2
gctctagatt acagcccttc ccggatcac                                     29

<210> SEQ ID NO 3
<211> LENGTH: 75
<212> TYPE: DNA
<213> ORGANISM: artificial sequence
<220> FEATURE:
<223> OTHER INFORMATION: primer 1 for pgi expression
```

-continued

```
<400> SEQUENCE: 3
atgaaaaaca tcaatccaac gcagaccgct gcctggcagg cactacagaa tggacagcaa    60
gcgaaccgga attgc                                                     75

<210> SEQ ID NO 4
<211> LENGTH: 74
<212> TYPE: DNA
<213> ORGANISM: artificial sequence
<220> FEATURE:
<223> OTHER INFORMATION: primer 2 for pgi expression

<400> SEQUENCE: 4
ttaaccgcgc cacgctttat agcggttaat cagaccattg gtcgagctat tcagaagaac    60
tcgtcaagaa ggcg                                                      74

<210> SEQ ID NO 5
<211> LENGTH: 75
<212> TYPE: DNA
<213> ORGANISM: artificial sequence
<220> FEATURE:
<223> OTHER INFORMATION: primer 1 for zwf expression

<400> SEQUENCE: 5
atggcggtaa cgcaaacagc ccaggcctgt gacctggtca ttttcggcgc tggacagcaa    60
gcgaaccgga attgc                                                     75

<210> SEQ ID NO 6
<211> LENGTH: 74
<212> TYPE: DNA
<213> ORGANISM: artificial sequence
<220> FEATURE:
<223> OTHER INFORMATION: primer 2 for zwf expression

<400> SEQUENCE: 6
ttactcaaac tcattccagg aacgaccatc acgggtaatc atcgccaccg tcagaagaac    60
tcgtcaagaa ggcg                                                      74

<210> SEQ ID NO 7
<211> LENGTH: 21
<212> TYPE: DNA
<213> ORGANISM: artificial sequence
<220> FEATURE:
<223> OTHER INFORMATION: primer 1 for pgm expression

<400> SEQUENCE: 7
cgcatccgac attttacggg c                                              21

<210> SEQ ID NO 8
<211> LENGTH: 21
<212> TYPE: DNA
<213> ORGANISM: artificial sequence
<220> FEATURE:
<223> OTHER INFORMATION: primer 2 for pgm expression

<400> SEQUENCE: 8
ttgcttgtgt cctttgtctg c                                              21

<210> SEQ ID NO 9
<211> LENGTH: 20
<212> TYPE: DNA
<213> ORGANISM: artificial sequence
<220> FEATURE:
<223> OTHER INFORMATION: primer 3 for pgm expression
```

```
<400> SEQUENCE: 9
cacatttaat aaaaaaaggg                                              20

<210> SEQ ID NO 10
<211> LENGTH: 21
<212> TYPE: DNA
<213> ORGANISM: artificial sequence
<220> FEATURE:
<223> OTHER INFORMATION: primer 4 for pgm expression

<400> SEQUENCE: 10
ccaaccggga tttaaaccga c                                            21

<210> SEQ ID NO 11
<211> LENGTH: 76
<212> TYPE: DNA
<213> ORGANISM: artificial sequence
<220> FEATURE:
<223> OTHER INFORMATION: primer 1 for pgi+zwf expression

<400> SEQUENCE: 11
atgaaaaaca tcaatccaac gcagaccgct gcctggcagg cactacagaa cagaataaat  60
aaatcctggt gtccct                                                  76

<210> SEQ ID NO 12
<211> LENGTH: 76
<212> TYPE: DNA
<213> ORGANISM: artificial sequence
<220> FEATURE:
<223> OTHER INFORMATION: primer 2 for pgi+zwf expression

<400> SEQUENCE: 12
ttaaccgcgc cacgctttat agcggttaat cagaccattg gtcgagctat atccgcttat  60
tatcacttat tcaggc                                                  76

<210> SEQ ID NO 13
<211> LENGTH: 20
<212> TYPE: DNA
<213> ORGANISM: artificial sequence
<220> FEATURE:
<223> OTHER INFORMATION: primer 1 for pgi+zwf+pgm expression

<400> SEQUENCE: 13
ttaccgtaac ggagtttaac                                              20

<210> SEQ ID NO 14
<211> LENGTH: 20
<212> TYPE: DNA
<213> ORGANISM: artificial sequnece
<220> FEATURE:
<223> OTHER INFORMATION: primer 2 for pgi+zwf+pgm expression

<400> SEQUENCE: 14
gcctcgtttc cctcatactg                                              20

<210> SEQ ID NO 15
<211> LENGTH: 21
<212> TYPE: DNA
<213> ORGANISM: artificial sequnece
<220> FEATURE:
<223> OTHER INFORMATION: primer 3 for pgi+zwf+pgm expression

<400> SEQUENCE: 15
```

```
ctgtctcttt aaaaagaaac c                                      21
```

<210> SEQ ID NO 16
<211> LENGTH: 18
<212> TYPE: DNA
<213> ORGANISM: artificial sequence
<220> FEATURE:
<223> OTHER INFORMATION: primer 4 for pgi+zwf+pgm expression

<400> SEQUENCE: 16

```
aatgaccgaa acgggtgg                                          18
```

<210> SEQ ID NO 17
<211> LENGTH: 30
<212> TYPE: DNA
<213> ORGANISM: artificial sequence
<220> FEATURE:
<223> OTHER INFORMATION: primer 1 for gapA promoter

<400> SEQUENCE: 17

```
cgcggatccg cgggaagagt gaggcgagtc                             30
```

<210> SEQ ID NO 18
<211> LENGTH: 19
<212> TYPE: DNA
<213> ORGANISM: artificial sequence
<220> FEATURE:
<223> OTHER INFORMATION: primer 2 for gapA promoter

<400> SEQUENCE: 18

```
atattccacc agctatttg                                         19
```

<210> SEQ ID NO 19
<211> LENGTH: 28
<212> TYPE: DNA
<213> ORGANISM: artificial sequence
<220> FEATURE:
<223> OTHER INFORMATION: primer 1 for gadA promoter

<400> SEQUENCE: 19

```
ctagtctaga gtcgttttc tgcttagg                                28
```

<210> SEQ ID NO 20
<211> LENGTH: 28
<212> TYPE: DNA
<213> ORGANISM: artificial sequence
<220> FEATURE:
<223> OTHER INFORMATION: primer 2 for gadA promoter

<400> SEQUENCE: 20

```
ttcgaactcc ttaaatttat ttgaaggc                               28
```

<210> SEQ ID NO 21
<211> LENGTH: 22
<212> TYPE: DNA
<213> ORGANISM: artificial sequence
<220> FEATURE:
<223> OTHER INFORMATION: prime 1 for aspA terminator

<400> SEQUENCE: 21

```
taacataacg ttgtaaaaac cg                                     22
```

<210> SEQ ID NO 22
<211> LENGTH: 28
<212> TYPE: DNA
<213> ORGANISM: artificial sequence

```
<220> FEATURE:
<223> OTHER INFORMATION: primer 2 for aspA terminator

<400> SEQUENCE: 22
cgcggatcct taagttgggt aacgccag                                              28
```

GENE EXPRESSION CASSETTE AND A TRANSFORMANT, AND A METHOD FOR MANUFACTURING 2-DEOXY-SCYLLO-INOSOSE AND A METHOD FOR PURIFYING 2-DEOXY-SCYLLO-INOSOSE USING SAID TRANSFORMANT

RELATED ART

The present invention relates to a gene expression cassette and a transformant, and a method for manufacturing 2-deoxy-scyllo-inosose and a method for purifying 2-deoxy-scyllo-inosose using the transformant.

PRIOR ART

The six-membered carbocyclic compound has been manufactured from petroleum as starting materials in petrochemistry. On the other hand, 2-deoxy-scyllo-inosose synthase (DOI synthase) was found in the butirosin-producer *Bacillus circulans*, wherein the 2-deoxy-scyllo-inosose synthase catalyzes a reaction of synthesizing 2-deoxy-scyllo-inosose (hereinafter, referred also to as DOI), which is one of six-membered carbocyclic compound, from glucose-6-phosphate (G-6-P) as a substrate (see FIG. 1, and Patent-related Document 1).

The DOI synthase is an enzyme involved in the biosynthesis of the aminoglycoside antibiotics containing 2-deoxystreptamine as an aglycon. DOI which is a product of the DOI synthase is a useful substance as starting materials for medicine and chemical-industrial resources. The method for chemically synthesizing DOI is necessary to employ the multi-step reaction, and use toxic or costly metals. On the other hand, by using the DOI synthase, it is possible to efficiently and shortly manufacture DOI. The method for shortly producing DOI from glucose-6-phosphate has been established, using a recombinant DOI synthase obtained from *E. coli* expressing the DOI synthase (see Patent-related document 1). Further, it is known that DOI can be synthesized by the two-steps enzyme reaction of acting glucose with hexokinase and the DOI synthase, or by the one-step enzyme reaction of acting glucose-6-phosphate with the DOI synthase (see Patent-related document 1, and Non-Patent-related document 1). In addition, it has been reported that DOI can be transformed into catechol by concentrating the enzymatic reacting solution and acting it with hydriodic acid in an acetic acid, without purifying DOI (see Patent-related document 1).

However, a method for synthesizing DOI with the fermentation from the biomass-derived D-glucose as starting materials using *E. coli* introduced the DOI synthase has not been proposed as an issue.

In addition, a method for purifying and isolating DOI itself has not still been reported, although it has been reported that DOI is synthesized by the enzymatic reaction and that DOI contained in the reaction mixture is transformed. Further, there is not any information involved in that DOI is purified from the nutrient medium of microorganism containing amino acids derived from peptone and several types of metallic ions in addition to several types and large amounts of constituent elements of any medium, and glucose as carbon source. That is, it has not been reported that DOI is purified under the circumstance of contaminating substances including the enzymatic reacting solution and the nutrient medium of microorganisms. Still more, it has never been established an industrially-applicable method for purifying DOI.

In order to purify DOI under the circumstance of the contaminating substance including the nutrient medium of microorganisms, a batch off by HPLC or a method using a charcoal column chromatography is known as laboratory methods. However, it goes without saying that the batch off by HPLC is not useful for an industrial production. In addition, in the method using the charcoal column chromatography, after organic compounds in the medium are adsorbed in the charcoal, it will be sequentially eluted by utilizing the difference of adsorbability of substances, with changing the concentration of organic solvents such as alcohols. Therefore, in the production of large amounts of DOI, it is necessary to use a large amount of charcoal enough to adsorb an enormous proportion of organic compounds in the medium. Accordingly, such a method is also unsuitable for a large-scale purification. For such reasons, it has not been established a suitable method for purifying DOI with an industrially-applicable method.

[Patent-related document 1] Japanese Patent Application Publication No. 2000-236881 (JPB3122762)

[Non-patent-related document 1] K. Kakinuma, E. Nango, F. Kudo, Y. Matsushima and T. Eguchi, Tetrahedron Letters, 2000, vol. 41, p. 1935-1938

[Non-patent-related document 2] Ota, Y. et al., J. Antibiot., 2000, vol. 53, p. 1158-1167

[Non-patent-related document 3] Kudo, F. et al., J. Antibiot., 1999, vol. 52, p. 559-571

DISCLOSURE OF THE INVENTION

A Problem to be Solved by the Invention

The present invention is made in view of the above-mentioned problems. That is, the present invention is to provide a gene expression cassette which enables a system for manufacturing DOI with industrial-scale, a transformant comprising the gene expression cassette, and a method for manufacturing 2-deoxy-scyllo-inosose and a method for purifying 2-deoxy-scyllo-inosose.

Means for Solving the Problem

The gene expression cassette according to the present invention is characterized in:

A gene expression cassette comprising a gene involved in a synthesis of 2-deoxy-scyllo-inosose.

In the gene expression cassette according to the present invention, said gene involved in a synthesis of 2-deoxy-scyllo-inosose is 2-deoxy-scyllo-inosose synthase. Herewith, it is possible to obtain a transformant which can industrially manufacture DOI In addition, the transformant according to the present invention is characterized in:

A transformant comprising the above-mentioned gene expression cassette transformed in a host cell.

In the transformant according to the present invention, said host cell is a host cell selected from the groups consisting of *Escherichia coli* and any of host cells stated in the GILSP genetically-modified microorganisms list on March, 2006. Herewith, it is possible to perform an industrial method for producing DOI.

In the transformant according to the present invention, said host cell is a host cell disrupted at least one of genes selected from the group consisting of pgi gene encoding phosphoglucose isomerase, zwf gene encoding glucose-6-phosphate 1-dehydrogenase, pgm gene encoding phosphoglucomutase and rmf gene encoding ribosome modulation factor involved in modification of protein synthesis during stationary phase. Herewith, it is possible to perform an industrial method for manufacturing DOI with high efficiency, in addition to the above-mentioned matter.

On the other hand, the method for manufacturing 2-deoxy-scyllo-inosose according to the present invention is characterized in:

A method for manufacturing 2-deoxy-scyllo-inosose comprising a step of contacting the above-mentioned transformant with carbon source. Herewith, it is possible to industrially manufacture DOI.

In the method for manufacturing 2-deoxy-scyllo-inosose according to the present invention, said carbon source is at least one type of carbon sources selected from the group consisting of D-glucose, oligosaccharide, polysaccharide, starch, cellulose, rice bran and molasses and biomasses capable of obtaining D-glucose. Herewith, it is possible to generally manufacture DOI, in addition to the above-mentioned matter.

The 2-deoxy-scyllo-inosose according to the present invention is characterized in:

A 2-deoxy-scyllo-inosose being obtained from the above-mentioned method for manufacturing 2-deoxy-scyllo-inosose. Herewith, it is possible to obtain 2-deoxy-scyllo-inosose with the attribute of the manufacturing method using the transformant.

Further, the method for purifying 2-deoxy-scyllo-inosose according to the present invention is characterized in:

A method for purifying 2-deoxy-scyllo-inosose comprising the steps of:

contacting the above-mentioned transformant with a carbon source to obtain a composition containing 2-deoxy-scyllo-inosose; and treating said composition with mixed bed column or double bed column comprising a hydrogen ion form of a strong-acid cation exchange resin and an organic acid ion form of a basic anion exchange resin. Herewith, it is possible to industrially obtain a highly purified DOI.

In the method for purifying 2-deoxy-scyllo-inosose according to the present invention, said organic acid ion form of the basic anion exchange resin is acetate ion form of anion exchange resin. Herewith, the method can be practically and preferably used, since acetic acid will be removed by concentration procedure.

The 2-deoxy-scyllo-inosose according to the present invention is characterized in:

A 2-deoxy-scyllo-inosose being obtained from the above-mentioned method for purifying 2-deoxy-scyllo-inosose. Herewith, it is possible to obtain a high purity of 2-deoxy-scyllo-inosose with the attribute of the manufacturing method using the transformant.

The method for purifying 2-deoxy-scyllo-inosose according to the present invention is characterized in:

A method for purifying 2-deoxy-scyllo-inosose comprising the steps of:

reacting the above-mentioned 2-deoxy-scyllo-inosose with trialkoxymethanes to obtain 2-deoxy-scyllo-inosose dialkylketals; and hydrolyzing said 2-deoxy-scyllo-inosose dialkylketals in the presence of acid. Herewith, it is possible to efficiently separate the contaminating substances, in addition to the above-mentioned matter.

In the method for purifying 2-deoxy-scyllo-inosose according to the present invention, said trialkoxymethanes are trimethoxymethane. Herewith, the method can be practically and preferably used, since methanol which will be formed in the following step of hydrolysis reaction can be easily removed by concentration procedure.

The 2-deoxy-scyllo-inosose according to the present invention is characterized:

A 2-deoxy-scyllo-inosose 2-deoxy-scyllo-inosose being obtained from the above-mentioned method for purifying 2-deoxy-scyllo-inosose. Herewith, it is possible to obtain 2-deoxy-scyllo-inosose which is practically superior in view of purity.

Effect of the Invention

The six-membered carbocyclic compound which is important for the starting material of medicine and industrial chemistry have been manufactured by the petroleum chemistry using the petroleum as starting materials. However, it is possible to synthesize 2-deoxy-scyllo-inosose being the six-membered carbocyclic compound from the regenerative biomass-derived D-glucose as starting materials by microorganisms, by means of using an art of the present invention. In addition, it is possible to restore purified DOI as treated with the culture medium.

BEST MODE FOR CARRYING OUT THE PRESENT INVENTION

Figure 1:
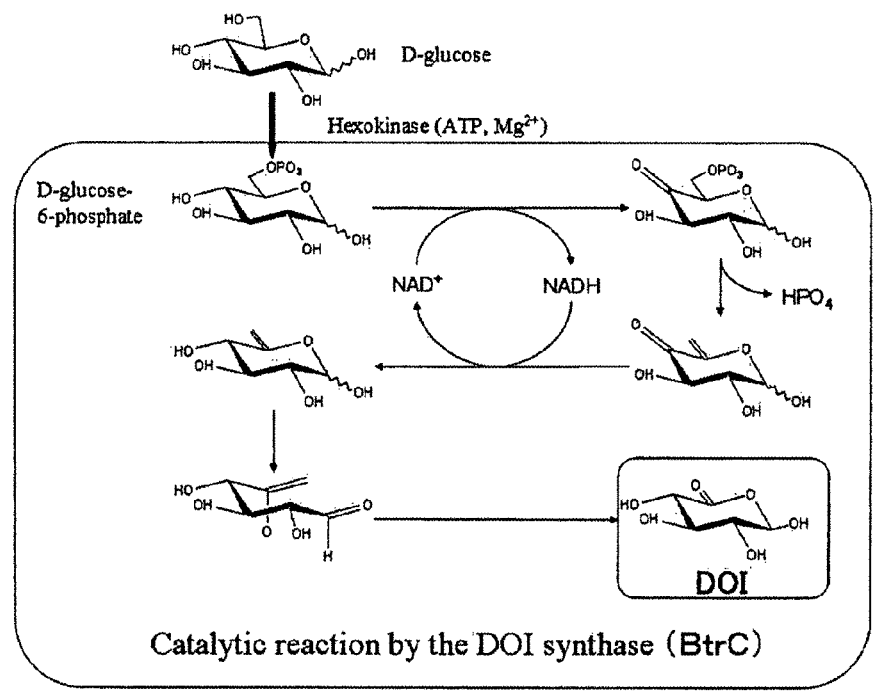
FIG. 1 is an illustration showing reaction pathways of forming DOI from D-glucose, and a reaction catalyzed by the DOI synthase.

In view of the property of the DOI synthase, there is a possibility that the useful resource DOI can be efficiently and shortly produced from the biomass-derived and abundant D-glucose as starting materials by means of microorganism as introduced the enzyme.

Here, the inventors were made the present invention, in order to develop a method for producing DOI by fermentation of *E. coli* as host cells with easy procedure and low cost, as a novel method for synthesizing DOI.

In addition, in the case that a system which industrially purify DOI will be considered, preferred examples of methods include several methods, one of which is to apply the culture medium containing DOI from top of a column and to elute off the purified DOI from the bottom of the column, the other of which is to crystallize DOI or DOI derivative and to separate thereof, and yet the other of which is combined said one of methods with said other of methods. In view of these, the present invention is made by means of searching column materials which adsorb substrates other than DOI, do not adsorb DOI and primarily elute off DOI, and by means of searching DOI derivatives which are capable of efficiently obtaining DOI after the crystallization and separation.

Reference will be made with regard to embodiments of the present invention.

<The Gene Expression Cassette According to the Present Invention>

The gene expression cassette according to the present invention is characterized in:

A gene expression cassette comprising a gene involved in a synthesis of 2-deoxy-scyllo-inosose. That is, the gene expression cassette according to the present invention is not limited, provided that the gene expression cassette according to the present invention comprises gene(s) involved in a synthesis of 2-deoxy-scyllo-inosose and gene(s) capable of expressing the gene involved in a synthesis of 2-deoxy-scyllo-inosose.

(The Gene Involved in a Synthesis of 2-Deoxy-Scyllo-Inosose)

In the gene expression cassette according to the present invention, the gene involved in a synthesis of 2-deoxy-scyllo-inosose may be a gene encoding the well-know proteins which synthesize the 2-deoxy-scyllo-inosose. The examples thereof includes btrC gene encoding 42 kDa subunit of the DOI synthase derived from *Bacillus circulans* wherein the DOI synthase synthesizes DOI from D-glucose (see Patent-related document 1, Non-patent-related document 2, and Genbank No. AB066276 etc.). Of course, genes derived from any organisms other than *Bacillus circulans* can be also utilized, provided that the genes encode an enzyme having an activity of synthesizing DOI. In addition, the nucleotide sequences of the above-mentioned genes may comprise any mutations including deletion, substitution and insertion of the nucleotide(s), provided that said genes are a gene expressing an enzyme having an activity of synthesizing DOI.

(Construction of the Gene Expression Cassette According to the Present Invention)

In construction of the gene expression cassette according to the present invention, a gene which can express the gene involved in the 2-deoxy-scyllo-inosose in the below-mentioned host cells may be used. The gene constitution of the gene expression cassette includes a promoter, sequence related to the transcriptional activation, RBS (ribosome binding site), and a terminator. For example, in a system for abundant expression of proteins in *E. coli* as host cells, DNA sequences including the promoter, the sequence related to the transcriptional activation and RBS (ribosome binding site) may be linked at 5'-upstream region of the gene, and DNA sequences including the terminator may be linked at 3'-downstream region of the gene. These DNA sequences may be used, as long as the sequences can properly act in *E. coli*. There is a promoter which constitutively or inductively expresses the target genes. Any promoters may be used in the present invention. The promoter that the expression of the target gene can be controlled is preferable. It should be noted that, in the gene expression in *E. coli* as host cells, high cost inducer(s) for the gene expression including IPTG (isopropyl-thio-galactopyranoside) have typically been used.

In the present invention, it is desirable that high expression system for the target gene is used, without using the above-mentioned high cost inducer such as IPTG. For this purpose, the expression system using the GAP promoter, the GAD promoter, the $P_L$ Expression System (Invitrogen) can be utilized.

In the $P_L$ Expression System, the gene expression introduced in the vector (pLEX, ampicillin-resistant marker) is controlled by the $P_L$ promoter which is derived from lambda phage and which constitutively and strongly induces the expression of the target gene. In addition, the $P_L$ Expression System is constituted such that the expression is controlled depending on the tryptophan concentration in the culture medium and that the expression is induced in the medium containing high concentration of tryptophan.

On the other hand, in the systems of either a system using gapA (a gene encoding glyceraldehyde-3-phosphate dehydrogenase A) promoter, or a system using gadA (a gene encoding glutamate decarboxylase A) promoter or a system using both promoters, the target gene introduced in the vector (pUC origin, ampicillin-resistant marker) is constitutively and strongly expressed in the logarithmic phase or the stationary phase of the cells. The expression system such as gapA promoter and gadA promoter is constituted such that the expression is induced in ordinary culture condition, without using the particular kinds of reagents and handlings.

On the other hand, in the $P_L$ Expression System, there are enough amounts of tryptophan in the complete medium as normally used in the culture of *E. coli* to induce the promoter activity. So, it is not necessary to further add tryptophan in order to induce the expression. In addition, it is not necessary to add the inducer for inducing the expression in the systems using gapA promoter or gadA promoter. That is, it is possible to highly express the target gene without using high cost inducer.

<The Transformant According to the Present Invention>

The transformant according to the present invention is characterized in:

A transformant comprising the above-mentioned gene expression cassette transformed in a host cell. Hereinafter, the host cells of the present invention will be explained.

(The Host Cells)

Host cells which can be used in the transformant according to the present invention are not limited, and any types of host cells can be used, including microorganisms which are deposited in depository institutions of strains such as IFO and ATCC. Examples include *E. coli*. In addition, the host cells as stated in GILSP (Good Industrial Large-Scale Practice) can be used, including the host cells as stated in GILSP on March, 2006 such as *Bacillus amyloliquefaciens*, *Bacillus brevis* HPD31, *Bacillus brevis* HPD31-M3, *Bacillus licheniformis* DN2461, *Bacillus licheniformis* DN2717, *Bacillus subtilis* K2A1, *Bacillus subtilis* Marburg 168, *Corynebacterium glutamicum*, *Escherichia coli* K12, *Geobacillus stearothermophilus*.

(The Gene-Disrupted Strain of the Present Invention)

In the transformant according to the present invention, the host cells as disrupted the chromosomal genes and/or the plasmid genes can be used, in view of the synthesis of the 2-deoxy-scyllo-inosose. In the preferred aspects of the present invention, either, both or all genes of pgi gene, zwf gene and pgm gene in the host cells, wherein these three gene are genes encoding phosphoglucose isomerase, glucose-6-phosphate 1-dehydrogenase and phosphoglucomutase, respectively and wherein these enzymes are relevant to the metabolism of glucose-6-phosphate, are disrupted (i.e. in the case that one of genes is disrupted, pgi gene, zwf gene, or pgm gene; in the case that two of genes are disrupted, pgi and zwf genes, or pgi and pgm genes; in the case that three of genes are disrupted, pgi, zwf and pgm genes). Further, in the preferred aspects of the present invention, the gene encoding RMF protein involved in modification of protein synthesis during stationary phase (rmf gene) in the host cells is singly disrupted, or the rmf gene in the above-mentioned strains which genes encoding enzymes relevant to the metabolism of glucose-6-phosphate is disrupted. This leads to the suppression of the degradation of glucose-6-phosphate, which is direct substrate for production of DOI, in the microorganisms. In addition, the productivity of DOI was dramatically increased due to the protein synthesis in the stationary phase.

[Gene-Disrupted Strain Wherein the Gene is Related to the Degradation of Glucose-6-Phosphate]

In order to synthesize DOI with possibly high yield, it is necessary to be considered to possibly suppress the catabolism of D-glucose in the microorganisms. In *E. coli*, genes encoding enzymes related to the catabolism of D-glucose include three genes wherein the genes are: pgi gene encoding phosphoglucose isomerase which relates to transform glucose-6-phosphate into fructose-6-phosphate in the glycolytic system; zwf gene encoding glucose-6-phosphate dehydrogenase which relates to transform glucose-6-phosphate into phosphogluconolactone in the pentose phosphate pathway; and pgm gene encoding phosphoglucomutase which relates to transform glucose-6-phosphate into glucose-1-phosphate. It can be considered that, by disrupting these genes, it is possible to suppress the catabolism of glucose-6-phosphate as substrate for the DOI synthase, along with the growth of the microorganisms.

[Gene-Disrupted Strain Wherein the Gene Relates to the Protein Synthesis During the Stationary Phase]

In order to cancel the prevention of the BtrC protein synthesis during the stationary phase, it can be considered that it is necessary to suppress the production of RMF protein related thereto. Here, it can be considered that rmf gene encoding RMF protein is disrupted to continue the synthesis of the BtrC protein after the stationary phase, thereby continuing the synthesis of DOI.

(Manufacture of the Gene-Disrupted Strain in the Present Invention)

In the present invention, the well-known method can be used for manufacturing the gene-disrupted strain in which the particular gene of the host cells is disrupted. For example, examples of such a method include a method for inducing the mutation (a method of natural breeding, addition of mutagen, UV irradiation, radiation), a method utilizing random mutation (methods using insertion sequence (IS) or transposon (Tn)) and the site-specific gene-disrupting method (single or double cross over method). Among these, it is preferable to use the site-specific gene-disrupting method which can insert fragments comprising the drug-resistant gene into the target gene, in view of screening to obtain the desired gene-disrupted strain. It should be noted that the host cells of the present invention is not limited as mentioned below, although the gene-disrupted host cells which are used for the transformant according to the present invention are manufactured by using Quick and Easy BAC Modification Kit (Gene Bridges).

(Method for Manufacturing the Transformant According to the Present Invention)

The transformant according to the present invention can be manufactured to introduce the above-mentioned gene expression cassette into the host cells. The method for introducing includes the competence method and endocytosis through any receptors.

<The Method for Manufacturing 2-Deoxy-Scyllo-Inosose According to the Present Invention>

The method for manufacturing 2-deoxy-scyllo-inosose according to the present invention is characterized to contact the above-mentioned transformant with a carbon source in any medium suitable to grow the transformant.

As the carbon source, D-glucose, nitrogen-containing monosaccharides such as D-glucosamine and D-galactosamine, and monosaccharides derived from sugars or oligosaccharides comprising two or more of monosaccharides, or carbohydrate (e.g. starch, rice bran and molasses) can be used.

As the medium for carrying out the method for manufacturing 2-deoxy-scyllo-inosose according to the present invention, the form of the medium such as solid medium, liquid medium is not limited, provided that the host cells can be proliferated and/or grown in the well-known medium. Examples of such medium include the agar medium, RMG medium, 2×YT medium, LB medium, M9 minimum medium and SOB medium. These medium may contain carbon sources, nitrogen sources, inorganic salts and other organic nutrient sources. The carbon sources may be as substances as set forth in Table 1 such as mannitol, in addition to the above-mentioned substances. Examples of the nitrogen sources include ammonium chloride, casamino acid, peptone and yeast extract. Examples of the inorganic salts include sodium hydrogen phosphate, potassium dihydrogen phosphate, magnesium chloride and sodium chloride. As mentioned above, it is not necessary to use the high cost inducer, in the case of using the GAP-GAD expression system and the $P_L$ Expression System (Invitrogen) as the host cells-vector system.

On the other hand, the medium may contain any suitable additives, depending on the growth of the host cells. In order to express the gene involved in the synthesis of the 2-deoxy-scyllo-inosose as introduced in the gene expression cassette, the medium may contain compounds increasing the promoter activity such as IPTG, tryptophan. Especially, the inducer may be added to the medium, in the case that the expression of the gene by the promoter is inducibly performed.

In the method for manufacturing 2-deoxy-scyllo-inosose according to the present invention, conditions of contacting the transformant with the carbon source, including temperature, duration and circumstance, are not limited, provided that the conditions are suitable for the growth of the transformant. For example, the temperature is more preferable in the range of 20 to 37° C. In addition, the duration may be in the range of 1 to 7 days, although the duration is not limited thereto.

For example, in the method for manufacturing 2-deoxy-scyllo-inosose according to the present invention, the transformant is firstly contacted with any materials being capable of being assimilated in E. coli as the carbon source. Thereafter, DOI is recovered from the obtained culture supernatant. In this way, it is possible to industrially obtain DOI by the method for manufacturing 2-deoxy-scyllo-inosose according to the present invention using the transformant.

DOI can be obtained with high yield from D-glucose by the actions of hexokinase and the DOI synthase, since the method for manufacturing 2-deoxy-scyllo-inosose according to the present invention has the above-mentioned constitution. In addition, by means of culturing the transformed strains including the GI724Δrmf transformed strain, the GI724ΔpgiΔrmf transformed strain, the GI724Δpgi transformed strain, the GI724ΔpgiΔzwf transformed strain and the GI724ΔpgiΔzwfΔpgm transformed strain comprising the above-mentioned plasmids of pGAP-btrC, pGAD-btrC, pGAP-btrC/pGAD-btrC and pLEX-btrC, DOI is produced from D-glucose via glucose-6-phosphate through five steps of reaction catalyzed by the DOI synthase, as shown in FIG. 1.

In the method for manufacturing 2-deoxy-scyllo-inosose according to the present invention, the transformant is contacted with the carbon source, thereby obtaining a composition comprising 2-deoxy-scyllo-inosose (e.g. the medium containing 2-deoxy-scyllo-inosose and the host cells). For example, DOI may be collected from the culture supernatant, in the case that the culture medium containing 2-deoxy-scyllo-inosose is used as the starting material of 2-deoxy-scyllo-inosose. In the present invention, as a method for recovering DOI from the culture solution, 2-deoxy-scyllo-inosose may be recovered by the well-known extraction method, in accordance with, for example, physical/chemical characteristics of 2-deoxy-scyllo-inosose and compositions of the culture medium. For example, the following method can be used. That is, after finishing the culture, the culture medium is firstly centrifuged by the centrifugal separator and the filtrator to remove the microorganism from the medium, thereby obtaining a culture supernatant. Thereafter, the culture supernatant is further filtrated to remove any solid materials including the microorganisms, the filtrate is applied to ion exchange resins and an elution is performed with the distilled water. Fractions not containing any impurities are collected through monitoring the refractive index, pH, the conductivity, and solvents of the so obtained solution are removed to recover DOI. Analysis of the so obtained DOI is performed by any methods including the high-performance liquid chromatography and the nuclear magnetic resonance method.

<First Aspect of the Method for Purifying 2-Deoxy-Scyllo-Inosose According to the Present Invention>

The method for purifying 2-deoxy-scyllo-inosose according to the present invention is characterized in:

A method for purifying 2-deoxy-scyllo-inosose comprising the steps of:

contacting the above-mentioned transformant with a carbon source to obtain a composition containing 2-deoxy-scyllo-inosose; and treating said composition with mixed bed column or double bed column comprising a hydrogen ion form of a strong-acid cation exchange resin and an organic acid ion form of a basic anion exchange resin. In the method for purifying 2-deoxy-scyllo-inosose according to the present invention, the step of contacting the transformant with the carbon source is performed in accordance with the method for manufacturing 2-deoxy-scyllo-inosose according to the present invention. This step will afford a composition containing 2-deoxy-scyllo-inosose. This composition comprises the above-mentioned medium. Hereinafter, reference will be made, in the case that culture medium is used as the above-mentioned medium.

There are several components of the culture medium in the culture solution after finishing the culture of the transformant in the medium containing the carbon source, in addition to the remained glucose as the carbon source. Examples of these several components include amino acids, peptides and metal ions. It is necessary to remove these several components in order to obtain DOI. The method for purifying 2-deoxy-scyllo-inosose according to the present invention will provide to solve the above-mentioned matter.

Impurities to be removed in the culture medium includes the remained D-glucose as the carbon source, amino acids, peptides and the metal ions, as mentioned above. It has found that it is possible to continue the culture until D-glucose is completely consumed, in accordance with the examination of the culture condition. Amino acids, peptides and metal ions were remained in the medium as the remained impurities. The amino acids include basic amino acids comprising a plurality of amino groups such as lysine, histidine and tryptophan, acidic amino acids comprising a plurality of carboxyl groups such as glutamic acid and aspartic acid. In addition, the metal ions include cations, and the counter ions including chloride ion and sulfate ion is present in the culture medium. Therefore, column materials will be searched such that all of such impurities are adsorbed on the material and DOI is not adsorbed on the material.

The present inventors have examined the search of the column material and condition for the elution, in accordance with such a concept. As the result, DOI was not purified in good yield with a method using general ion exchange resins including sodium ion or hydrogen ion form of strong-acid cation exchange resin and chloride ion or hydroxylate ion form of basic anion exchange resin. That is, the above-mentioned purpose cannot be achieved by using a double bed column connecting the above-mentioned resins or a mixed bed column by mixing the resins. Amino acids bind to either of the above-mentioned two ion exchange resins. In addition, metal ions bind to the cation exchange resin, while DOI has a property of not binding both of the exchange resins since DOI does not have ionic functional groups. Therefore, it can be presumed that the amino acids and the metallic salts bind to the ion exchange resins, and DOI is eluted off without being adsorbed. However, the obtained result is not so. The yield of DOI was lower than 50%, and the yield was greatly changed depending on the used conditions of the ion exchange resin. More yields and stable performances are required in order to fit an industrial method in mass scale.

The present inventors have further examined the column material and the conditions for the purification. As the result, the present inventors have found that DOI can be efficiently purified by using the mixed bed column or double bed column comprising organic acid ion as counter ion of the anion exchange resin, that is, organic acid ion form of basic anion exchange resin and hydrogen ion form of strong-acid cation exchange resin. Examples of the organic acid include acetic acid, propionic acid and oxalic acid, especially, acetic acid is preferably used. Acetic acid as the organic acid is preferably used, since DOI is easily and extremely degraded over pH 8, and DOI is only stable in the weak acidic range of pH 3 to 5. That is, if DOI was completely stable at both ranges of acidic range and basic range, it would be possible to remove the impurities, even in a method to elute the culture medium through the double bed column of separate columns filled with the anion exchange resin and the cation exchange resin as generally-used. In addition, it would be possible to purify DOI with the mixed bed column in the both ranges if DOI had similar stability to that of fructose. The present inventors are the first person who found that DOI is unstable in the alkaline range such that DOI is degraded even by using the mixed bed column along with the double bed column.

In order to solve this problem, the present inventors have examined a selection of the counter ion binding to the ion exchanged resin to be used. As the result, the present inventors have found a method using the organic acid ion as the counter ion for the anion exchange resin. This will lead that the organic acid is remained in the eluent and is contaminated in fractions containing DOI. This is effective to maintain pH of the eluent as around 4. Among the organic acid, acetic acid has an advantage of capable of being removed by the concentration procedure.

It has found that DOI can be purified by means of passing the culture solution through an ion exchange column comprising a mixture of hydrogen form of cation exchange resin and organic acid ion form of anion exchange resin. Therefore, the present invention has been completed. This is a desired method for industrially manufacturing in mass scale.

Charged impurities, amino acids, peptides and metal ions which are derived from starting materials as remained in the culture medium which has completely consumed glucose can be adsorbed and removed in the method for purifying using mixed bed or double bed form of ion exchange resin column. Therefore, DOI which is neutral and is not adsorbed can be eluted off to purify it. It should be noted that there is a possibility to contaminate any neutral materials into the fraction containing DOI, depending on the condition of the culture. Accordingly, a further purification method of DOI was examined to obtain the highly purified DOI eluted off from the ion exchange column. It is presumed that DOI is an equilibrium mixture of keto and hydrate forms, on the basis of NMR analysis. So, it can be understood that it is difficult to crystallize DOI. It has not been reported the crystallization of DOI and DOI derivatives. Hereinafter, a method for highly purifying DOI will be described.

<Second Aspect of the Method for Purifying 2-Deoxy-Scyllo-Inosose According to the Present Invention>

The method for purifying 2-deoxy-scyllo-inosose according to the present invention is characterized in:

A method for purifying 2-deoxy-scyllo-inosose comprising the steps of:

reacting the above-mentioned 2-deoxy-scyllo-inosose with trialkoxymethanes to obtain 2-deoxy-scyllo-inosose dialkylketals; and hydrolyzing said 2-deoxy-scyllo-inosose dialkylketals in the presence of acid. Examples of the 2-deoxy-scyllo-inosose which can be used in this aspect of the present invention include the 2-deoxy-scyllo-inosose as obtained in the first aspect of the present invention, in addition to the above-mentioned composition containing 2-deoxy-scyllo-inosose. Hereinafter, the second aspect will be described.

Figure 14:
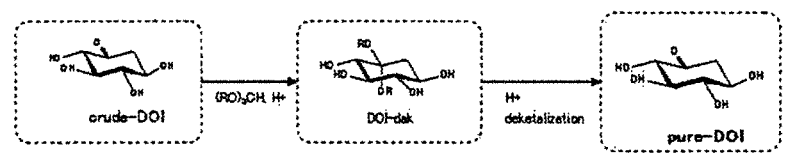
FIG. 14 is an illustration showing a principle of the second aspect of the method for purifying 2-deoxy-scyllo-inosose according to the present invention.

The present inventors have examined the search of materials and the examination of a method for purifying complying with a principle wherein the principle is based on that DOI as eluted is converted into crystallizable material(s), the materials is crystallized, the crystallized material is separated and purified, and the crystallizable material is efficiently restored into DOI. FIG. 14 shows an illustration of the principle. FIG. 14 is an illustration showing a principle of the second aspect of the method for purifying 2-deoxy-scyllo-inosose according to the present invention.

In order to comply with these requirements, it is necessary that reactions for converting DOI and for restoring it into DOI can be performed in an acidic condition which does not degrade DOI, that the material(s) as converted derivative is easily crystallized and restored into DOI, and that these procedure(s) can be industrially performed. It has been examined several methods complying with these requirements. As the result, it has been found that a method for reacting DOI with alkoxymethanes in an acidic condition in which DOI is stable to convert it into 2-deoxy-scyllo-inosose dialkylketals (DOI-dak), and for crystallizing and purifying DOI-dak.

In alkoxymethane ($(RO)_3CH$), examples of R are not limited, provided that examples include alkanes having 1 to 4 of carbon atoms, such as methane, ethane, propane and butane. In the present invention, a most preferable example of trialkoxymethanes is trimethoxymethane, since an alcohol which is formed in the following step of hydrolyzing can be easily removed. It should be noted that deoxy-scyllo-inosose dimethylketal (DOI-dmk) will be obtained in the case of using trimethoxymethane.

The crystallization of 2-deoxy-scyllo-inosose alkylketals may be performed such that 2-deoxy-scyllo-inosose alkylketals are dissolved in an appropriate solvent (e.g. methanol, ethanol and water), and a liquid medium which decrease the hydrophilicity of the liquid phase thereof (e.g. chloroform, hexane and ethers) is used. So, crystals of 2-deoxy-scyllo-inosose alkylketals will be obtained.

The so obtained 2-deoxy-scyllo-inosose alkylketals will be hydrolyzed in the presence of acid to be restored into 2-deoxy-scyllo-inosose. The hydrolysis reaction may be performed in an appropriate catalyst such as p-toluenesulfonic acid, hydrochloric acid and sulfuric acid. After hydrolysis, 2-deoxy-scyllo-inosose will be obtained.

Therefore, the method for purifying 2-deoxy-scyllo-inosose according to the present invention is a desirable method for industrial manufacturing in mass scale.

Embodiment

An explanation will be made with regard to the present invention in accordance with embodiments. It should be noted that the scope of the present invention is not limited to these embodiments.

Example 1

DOI Synthase Gene btrC gene was utilized for hydrocarbon-cyclizing enzyme gene wherein the btrC gene encodes 42 kDa subunit protein of 2-deoxy-scyllo-inosose (DOI) synthase derived from *Bacillus circulans* (see Patent-related document 1, Genbank No. AB066276 and Non-patent-related document 2).

Example 2

Construction of Recombinant Plasmid and Recombinant Strain

<btrC Gene and pLEX-btrC>

Figure 2A:
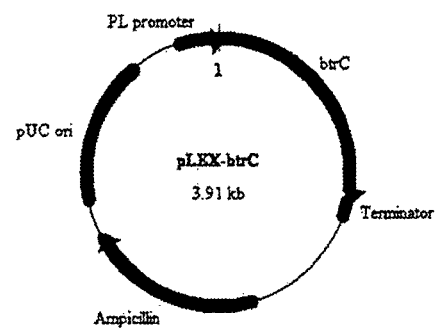
FIG. 2A is an illustration showing the structure of pLEX-btrC.
Figure 2B:
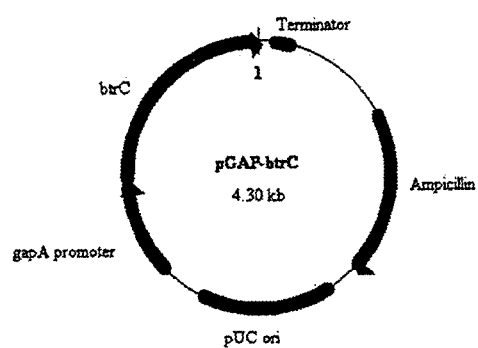
FIG. 2B is an illustration showing the structure of pGAP-btrC.
Figure 2C:
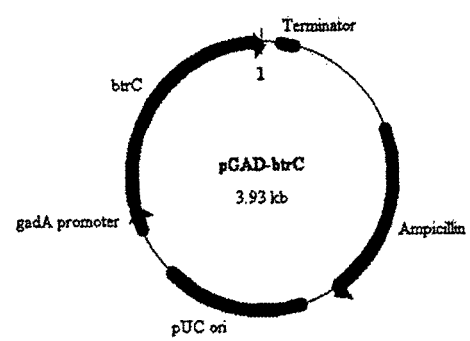
FIG. 2C is an illustration showing the structure of pGAD-btrC.
Figure 2D:
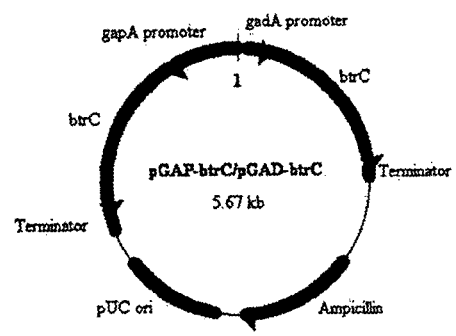
FIG. 2D is an illustration showing the structure of pGAP-btrC/pGAD-btrC.

Plasmid pDS4 comprising full length of btrC gene (Non-patent-related document 3) as the template, primer 1 stated as Sequence No. 1, and primer 2 stated as Sequence No. 2 were used. KOD polymerase (Toyobo) was used for PCR amplification of btrC gene. 30 cycles of PCR reaction were performed wherein the cycle consists of a cycle of reacting at 94° C. for 30 seconds, at 52° C. for 30 seconds and 68° C. for 1 minute. DNA fragment so obtained by the PCR amplification was digested with Nde I and XbaI, and was inserted into the NdeI-XbaI site of the multicloning site located on a vector pLEX to constitute pLEX-btrC (FIG. 2A).

<pGAP-btrC/p-GAD-btrC>

A gapA promoter gene was PCR-amplified with chromosomal DNA of *E. coli* as the template and a primer stated as Sequence No. 17 and a primer stated as Sequence No. 18. The PCR amplification of the gapA promoter gene was performed with KOD polymerase in the following reacting condition to obtain the gapA promoter fragments.

30 cycles, the cycle of reacting:
at 94° C. for 30 seconds;
at 50° C. for 30 seconds; and
at 68° C. for 1 minute A gadA promoter gene was PCR-amplified with chromosomal DNA of *E. coli* as the template, a primer stated as Sequence No. 19 and a primer stated as Sequence No. 20. The PCR amplification of the gadA promoter gene was performed with KOD polymerase in the following reacting condition to obtain the gadA promoter fragments.

30 cycles, the cycle of reacting:
at 94° C. for 30 seconds;
at 52° C. for 30 seconds; and
at 68° C. for 1 minute A aspA terminator gene was PCR-amplified with a plasmid pLEX (invitrogen) comprising the aspA terminator gene as the template and a primer stated as Sequence No. 21 and a primer stated as Sequence No. 22. The PCR amplification of the aspA promoter gene was performed with KOD polymerase (TOYOBO) in the following reacting condition to obtain the aspA terminator fragments.

30 cycles, the cycle of reacting:
at 94° C. for 30 seconds;
at 55° C. for 30 seconds; and
at 68° C. for 1 minute The PCR-amplified gadA promoter fragments were reacted with the above-mentioned btrC fragment at 16° C. for 30 minutes, using 2× Ligation mix (TAKARA). The so obtained ligation product as the template, a primer stated as Sequence No. 2 and a primer stated as Sequence No. 5 were used to be PCR-amplified, using KOD polymerase, in the following conditions, thereby obtaining a gadA-btrC fragment ligated with the above-mentioned two fragments.

30 cycles, the cycle of reacting:
at 94° C. for 30 seconds;
at 52° C. for 30 seconds; and
at 68° C. for 1 minute Digested fragment with XbaI was inserted into XbaI site of the multicloning site located on the vector pLEX (Invitrogen).

Next, the PCR-amplified gapA promoter fragments were reacted with the above-mentioned btrC fragment and the aspA terminator fragment at 16° C. for 30 minutes, using the 2× Ligation mix. The so obtained ligation product as the template, a primer stated as Sequence No. 8 were used to be PCR-amplified, using KOD polymerase, in the following conditions, thereby obtaining a gapA promoter-btrC-aspA terminator fragment ligated with the above-mentioned three fragments.

Figure 5:
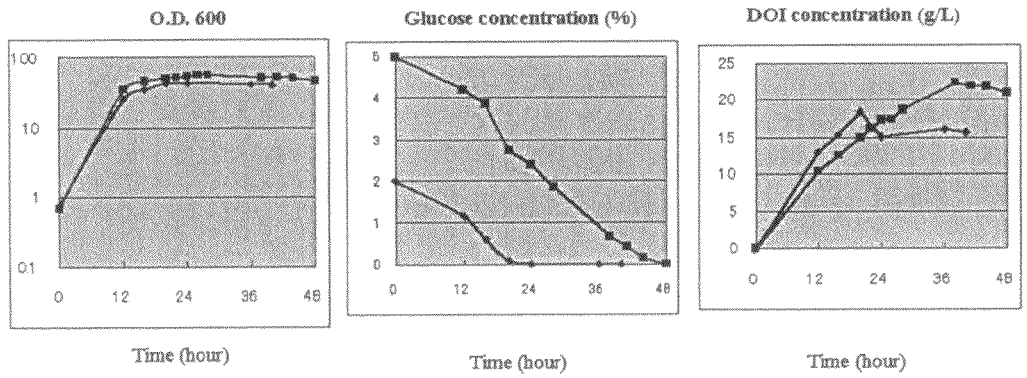
FIG. 5 is a graph showing time courses of (A) turbidity of the medium, (B) D-glucose concentration and (C) DOI production during the culture of the *E. coli* GI724Δpgi strain comprising pLEX-btrC (2×YT medium+2% glucose (♦) or 2×YT+5% glucose (■), 3 L, 30° C., pH 7.5) (the horizontal axes correspond to the elapsed time after addition of glucose).

30 cycles, the cycle of reacting:
at 94° C. for 30 seconds;
at 50° C. for 30 seconds; and
at 68° C. for 1 minute Digested fragment with BamHI was inserted into BamHI site of the multicloning site located on the vector pLEX (Invitrogen) which was inserted the gadA-btrC to constitute pGAP-btrC/pGAD-btrC (FIG. 5).

Example 3

Preparation of Host Cells

The disruption of genes was performed with Quick and Easy BAC Modification Kit (Gene Bridges), in accordance with the method as stated in the manufacturer's protocol of the kit. Sequences of primer sets for PCR which are used to manufacture the cassette using the single disruption of the pgi gene are shown in Sequence No. 3 and Sequence No. 4. Sequences of primer sets for the amplification of the cassette using the single disruption of the zwf gene are shown in Sequence No. 5 and Sequence No. 6. Sequences of primer sets for manufacturing the cassette using the single disruption of the pgm gene are shown in Sequence No. 7, Sequence No. 8, Sequence No. 9 and Sequence No. 10. Sequences of primer sets which are used to amplify the cassette for disrupting the pgi gene against the single-gene-disrupted strain of the zwf gene for obtaining the double gene-disrupted strain of the pgi and zwf genes are shown in Sequence No. 11 and Sequence No. 12. Sequences of primer sets which are used to amplify the cassette for disrupting the pgm gene against the single-gene-disrupted strain of the pgi gene for obtaining the double gene-disrupted strain of the pgi and pgm genes are shown in Sequence No. 7, Sequence No. 8, Sequence No. 9 and Sequence No. 10. Further, sequences of primer sets which are used to amplify the cassette for disrupting the zwf gene against the double gene-disrupted strain of the pgi and pgm genes for obtaining the triple gene-disrupted strain of the pgi, zwf and pgm genes are shown in Sequence No. 5 and Sequence No. 6. In addition, sequences of primers for a disruption cassette of the rmf gene are shown in Sequence No. 13, Sequence No. 14, Sequence No. 15 and Sequence No. 16.

A vector pSC101-BAD-gbaA-tetra was introduced into *E. coli* as the host cells, wherein the vector encodes group of enzymes which enhance the homologous recombination in *E. coli* (GI724), as enclosed in the Kit. The strain d in the LB medium supplemented with 3 μg/ml of tetracycline for overnight. Precultured microorganisms were inoculated in the LB medium added with 3 μg/ml of tetracycline at 1% concentration, and then grown at 30 until O.D.=0.2. At the time, arabinose was added at final concentration of 0.2%, and further cultured at 37° C. for 1 hour to inductively express the group of enzymes involved in the enhancement of the homologous recombination. Further, the transformation was performed with the cassette for the gene disruption to induce the gene disruption for the target genes. The so obtained transformant was selected at 37° C. with the LB medium supplemented with one, two or three of chloramphenicol, neomycin (kanamycin) or streptomycin to obtain the desired gene-disrupted strains including pgi gene-disrupted strain (Δpgi strain), zwf gene-disrupted strain (Δzwf strain), pgm gene-disrupted strain (Δpgm strain), pgi/zwf double gene-disrupted strain (ΔpgiΔzwf strain), pgi/pgm double-gene disrupted strain (ΔpgiΔpgm strain) and pgi/zwf/pgm triple gene-disrupted strain (ΔpgiΔzwfΔpgm strain). rmf gene-disrupted strains for each of the above-mentioned gene-disrupted strains were obtained in accordance with the above-mentioned procedure. Growth and development of wild type strain and each of gene-disrupted strains in any one of the carbon sources are shown in Table 1.

The growth rates of the Δpgi, Δzwf and Δpgm strains were remarkably delayed in comparison with the wile type, even though these gene-disrupted strains can utilize glucose as the carbon source. It can be understood that the consumption of D-glucose is suppressed in the microorganisms. In addition, the growth of the ΔpgiΔzwf, ΔpgiΔpgm and ΔpgiΔzwfΔpgm strains were extremely difficult in the medium containing D-glucose as the single carbon source. It can be understood that the degradation of glucose-6-phosphate is almost completely suppressed. This will promise that DOI production and the conversion rate into DOI are more increased in comparison with the wild type, by means of using these gene-disrupted strains. In addition, it is possible to improve the growth of the double- and triple-gene disrupted strains by supplementarily adding non-fermented carbon source such as mannitol and gluconate (see Table 1). In addition, with regard to the carbon source in the rmf-gene disrupted strain, the same growth was observed similar to the strains in which the glucose-6-phosphate metabolic enzyme genes were disrupted.

TABLE 1

| carbon source | wild type | Δpgi | Δzwf | Δpgm | ΔpgiΔzwf | ΔpgiΔpgm | ΔpgiΔzwfΔpgm |
|---|---|---|---|---|---|---|---|
| D-glucose | ++ | + | ++ | ++ | − | − | − |
| fructose | ++ | ++ | ++ | ++ | + | + | + |
| glycerol | +/− | + | ++ | ++ | + | + | + |
| mannitol | ++ | + | ++ | ++ | ++ | ++ | ++ |
| gluconate | − | ++ | ++ | ++ | ++ | ++ | ++ |

(In table 1,
a mark "++" indicates that the cells are extremely grown,
a mark "+" indicates that the cells are well grown,
a mark "+/−" indicates that the cells are slightly grown, and
a mark "−" indicates that the cells are less grown.)

Example 4

The Transformant

The host cells of *E. coli* (GI724) were transformed with pLEC-btrC as obtained, and selected in the medium containing ampicillin to obtain GI724/pLEX-btrC strain, in accordance with the protocol as stated in the manufacturer's protocol of the Kit made by Gene Bridges. In addition, the host cells of *E. coli* (GI724) were transformed with pGAP-btrC/pGAD-btrC as obtained, and selected in the medium containing ampicillin to obtain GI724/pGAP-btrC/pGAD-btrC strain, in a similar way. Further, several strains which were gene-disrupted including GI724Δrmf, GI724Δpgi, GI724Δzwf, GI724Δpgm, GI724ΔpgiΔrmf, GI724ΔpgiΔzwf, GI724ΔpgiΔpgm and GI724ΔpgiΔzwfΔpgm were also transformed with pGAP-btrC/pGAD-btrC to obtain GI724Δrmf/pGAP-btrC/pGAD-btrC strain, GI724Δpgi/pGAP-btrC/pGAD-btrC strain, GI724Δzwf/pGAP-btrC/pGAD-btrC strain, GI724Δpgm/pGAP-btrC/pGAD-btrC strain, GI724ΔpgiΔrmf/pGAP-btrC/pGAD-btrC strain, GI724ΔpgiΔzwf/pGAP-btrC/pGAD-btrC strain, GI724ΔpgiΔpgm/pGAP-btrC/pGAD-btrC strain and GI724ΔpgiΔzwfΔpgm/pGAP-btrC/pGAD-btrC strain.

Example 5

Confirmation for the Expression of the DOI Synthase

<GI724Δpgi/pLEX-btrC Strain>

Figure 3A:
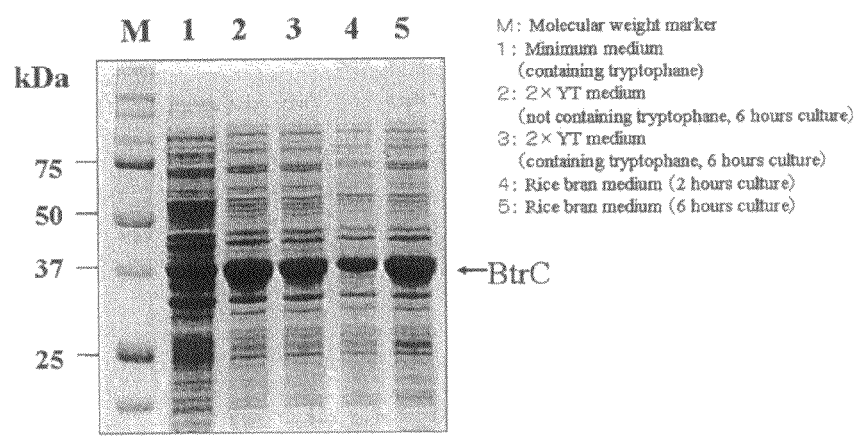
FIG. 3A is a view showing a SDS-PAGE pattern of cell extracts from the *E. coli* GI724 Δpgi strain comprising pLEX-btrC in the case of the strain cultured in 2×YT medium or the rice bran medium at the indicated time points.

The GI724Δpgi/pLEX-btrC strain was grown at 30° C. in an induction medium (6% sodium hydrogen phosphate, 3% potassium dihydrogen phosphate, 0.5% sodium chloride, 1% ammonium chloride, 0.2% casamino acid, 0.5% D-glucose, 1 mM magnesium chloride) until O.D. 600 nm was reached to 0.7. Then, the stain was transferred into 2×YT medium (complete medium for *E. coli*, 1.6% tryptophan, 1% yeast extract, 0.5% sodium chloride) and further cultured 37° C. for 6 hours. Then, the strain was collected. The expression of BtrC protein was confirmed with 12% SDS polyacrylamide gel electrophoresis. The result is shown in FIG. 3A. It was confirmed that the BtrC protein were abundantly expressed in the culture of 2×YT medium for 6 hours. It should be noted that the following items were electrophored in each lane of FIG. 3A.

Lane M:

Molecular weight marker (Precision Plus Protein Standards (BIO-RAD), Catalog No. 161-0374, hereinafter, by the same token)

Lane 1:

Cell extract with 1×SDS Loading buffer (hereinafter, by the same token) from the strain after the culture of GI724 strain comprising pLEX-btrC for 6 hours in the minimum nutritive medium (0.6% sodium hydrogen phosphate, 0.3% potassium dihydrogen phosphate, 0.05% sodium chloride, 0.1% ammonium chloride) (1×SDS Loading Buffer: 50 mM Tris-HCl (pH 6.8); 2% SDS; 0.1% Bromophenolblue; 10% Glycerol; 100 mM Dithiothreitol solution)

Lane 2:

Cell extract from the strains after the culture of GI724 strain comprising pLEX-btrC for 6 hours in the induction medium supplemented with tryptophan Lane 3:

Cell extract from the strains after the culture of GI724 strain comprising pLEX-btrC for 6 hours in the induction medium not supplemented with tryptophan Lane 4:

Cell extract from the strains after the culture for 2 hours in a rice bran medium (composition: containing 20% of rice bran treated with an enzyme)

Lane 5:

Cell extract from the strains after the culture for 6 hours in a rice bran medium (composition: containing 20% of rice bran treated with an enzyme) supplemented with tryptophan The BtrC protein was abundantly expressed in the strain cultured in the 2×YT medium even though the medium was not supplemented with tryptophan. In addition, the BtrC protein was abundantly expressed in the strain cultured in the rice bran medium. Therefore, it was shown that the DOI synthase gene can be highly expressed in these expression systems without using the high cost inducer.

The GI724ΔpgiΔzwfΔpgm/pGAP-btrC/pGAD-btrC Strain>

Figure 3B:
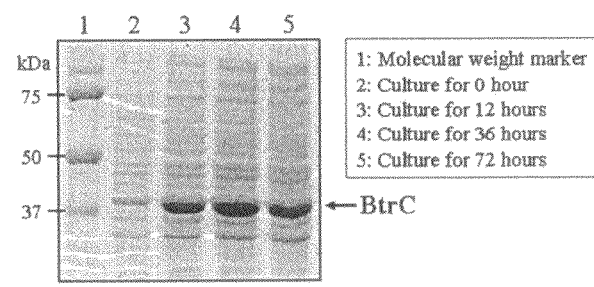
FIG. 3B is a view showing a SDS-PAGE pattern of cell extracts from the *E. coli* GI724ΔpgiΔzwfΔpgm strain comprising pGAP-btrC/pGAD-btrC in the case of the strain cultured in 2×YT medium at the indicated time points.

The GI724ΔpgiΔzwfΔpgm/pGAP-btrC/pGAD-btrC strain was cultured in a pre-culture medium (0.6% disodium hydrogen phosphate, 0.3% potassium dihydrogen phosphate, 0.05% sodium chloride, 0.1% ammonium chloride, 2% casamino acid, 1% glycerin, 1 mM magnesium chloride) at 30° C. for overnight. 1% of the strain in the pre-culture medium were added in 2×YT medium (complete medium for E. coli, 1.6% tryptone, 1% yeast extract, 0.5% sodium chloride) and cultured at 30° C. until O.D. 600 nm was reached to 0.7. Then, the strain was collected. The expression of BtrC protein was confirmed with 12% SDS polyacrylamide gel electrophoresis. The result is shown in FIG. 3B. It should be noted that the following items were electrophored in each lane of FIG. 3B.

Lane 1: Molecular weight marker

Lane 2: Cell extract of the strain obtained from the culture at 0 hour

Lane 3: Cell extract of the strain obtained from the culture after 12 hours

Lane 4: Cell extract of the strain obtained from the culture after 36 hours

Lane 5: Cell extract of the strain obtained from the culture after 72 hours

It was confirmed that the BtrC protein was abundantly expressed in the strain cultured in the 2×YT medium for 6 hours, as shown in FIG. 3B. Therefore, it was shown that the DOI synthase gene can be highly expressed in these expression systems without using the high cost inducer.

Example 6

Synthesis of DOI

<Synthesis of DOI Using the GI724Δpgi Strain Comprising pLEX-btrC>

The GI724Δpgi/pLEX-btrC strain was inoculated in 35 mL of a pre-culture solution (RMG medium, 0.6% sodium hydrogen phosphate, 0.3% potassium dihydrogen phosphate, 0.05% sodium chloride, 0.1% ammonium chloride, 2% casamino acid, 1% glycerin, 1 mM magnesium chloride) contained in 300 mL conical flask, and cultured for 15 hours. Next, 1% of the strain was inoculated in 3 L of 2×YT medium contained in 10 L of jarfermenter. The strain was cultured in a condition of 30° C. of culture temperature, 300 rpm of mixing speed, 10 L air per minute and pH 7.7 until O.D. 600 nm was reached to 0.7, and then 2% or 5% of D-glucose was added in the culture, and the strain was further cultured for 48 hours. The culture solution at the indicated time points was centrifuged to remove the strain, thereby collecting a culture supernatant 1.

<Synthesis of DOI Using the GI724ΔpgiΔZwf Strain Comprising pLEX-btrC>

The GI724Δpgiwf/pLEX-btrC strain was inoculated in 35 mL of a RMG medium containing 1% mannitol (0.6% sodium hydrogen phosphate, 0.3% potassium dihydrogen phosphate, 0.05% sodium chloride, 0.1% ammonium chloride, 2% casamino acid, 1% glycerin, 1 mM magnesium chloride), and cultured for overnight. Next, 1% of the strain was inoculated in 3 L of 2×YT medium containing 3% mannitol contained in 10 L jarfermenter, and were cultured in a condition of 30° C. of culture temperature, 300 rpm of mixing speed, 10 L air per minute and pH 7.7 until O.D. 600 nm was reached to 0.7, and then 3% of D-glucose was added in the culture, and the culture was continued. The culture solution at the indicated time points was centrifuged to remove the strain, thereby collecting a culture supernatant 2.

<Synthesis of DOI Using the GI724ΔpgiΔzwfΔpgm Strain Comprising pLEX-btrC>

The GI724ΔpgiΔzwfΔpgm strain comprising pLEX-btrC was inoculated in 50 mL of a preculture medium contained in 300 mL conical flask (0.6% disodium hydrogen phosphate, 0.3% potassium dihydrogen phosphate, 0.05% sodium chloride, 0.1% ammonium chloride, 2% casamino acid, 1% glycerol, 1 mM magnesium chloride), and cultured for 15 hours. Next, 1% of the strain of the preculture solution was inoculated in 3 L of 2×YT medium contained in 10 L jarfermenter (MDL-6C, made by Marubishi Bioengineering). The strain was cultured in a condition of 25° C. of culture temperature, 300 rpm of mixing speed, 10 L air per minute and pH 7.0 until O.D. 600 nm was reached to 0.7, and then 5% of D-glucose was added in the culture, and the culture was further cultured for 72 hours. The culture solution at the indicated time points time was centrifuged to remove the strain, thereby collecting a culture supernatant 3.

<Synthesis of DOI Using the GI724ΔpgiΔzwfΔpgm Strain Comprising pGAP-btrC/pGAD-btrC>

The GI724ΔpgiΔzwfΔpgm strain comprising pGAP-btrC/pGAD-btrC was inoculated in 50 mL of a preculture solution contained in 300 mL conical flask (0.6% disodium hydrogen phosphate, 0.3% potassium dihydrogen phosphate, 0.05% sodium chloride, 0.1% ammonium chloride, 2% casamino acid, 1% glycerol, 1 mM magnesium chloride), and cultured for 15 hours. Next, 1% of the strain of the preculture solution was inoculated in 3 L of 2×YT medium contained in 10 L jarfermenter, and was cultured in a condition of 25° C. of culture temperature, 300 rpm of mixing speed, 10 L air per minute and pH 6.0 until O.D. 600 nm was reached to 0.7, and then 5% of D-glucose was added in the culture, and the culture was further cultured for 72 hours. The culture solution at the indicated time points was centrifuged to remove the strain, thereby collecting a culture supernatant 4.

<Synthesis of DOI Using the GI724Δrmf Strain Comprising pLEX-btrC>

The GI724Δrmf strain comprising pLEX-btrC was inoculated in 3 mL of a preculture solution contained in test tube (0.6% disodium hydrogen phosphate, 0.3% potassium dihydrogen phosphate, 0.05% sodium chloride, 0.1% ammonium chloride, 2% casamino acid, 1% glycerol, 1 mM magnesium chloride), and cultured for 15 hours. 1% of the strain of the preculture solution was inoculated in 10 mL of 2×YT medium contained in L-shaped test tube. The strain was cultured in a condition of 30° C. of culture temperature, 160 rpm of mixing speed and pH 7.0 until O.D. 600 nm was reached to 0.7, and then 3% of D-glucose was added in the culture, and the culture was further cultured for 72 hours. The culture solution at the indicated time points was centrifuged to remove the strain, thereby collecting a culture supernatant 5.

Example 7

Measurement of DOI Production

<Oximation of DOI>

Measurement of DOI accumulated in the culture supernatant was performed as follows. That is, with regard to the culture supernatants 1 and 2, the culture solution(s) at the indicated time points were collected. One volume of water, two volumes of methanol and 1.5 mg/ml of O-(4-nitrobenzyl) hydroxylamine (NBHA), with regard to the volume of the supernatant(s) were added to the supernatant(s) and mixed, and incubated at 60° C. for 1 hour to obtain oxime derivative of DOI.

With regard to the culture supernatants 3, 4 and 5, 9 volumes of distilled water was added to the supernatant(s), and added one volume of methanol with regard to this solution, and then 30 mg/ml of O-(4-nitrobenzyl)hydroxylamine hydrochloride salt (NBHA) was added and mixed, and incubated at 60° C. for 1 hour to obtain oxime derivative of DOI.

<Detection of DOI>

The solvent was evaporated from the oxime of DOI so obtained with SpeedVac System (ISS110, made by Thermo), the obtained oxime derivative of DOI was dissolved in an appropriate volume of methanol, the aliquot was analyzed with HPLC (high-performance liquid chromatography) to perform the detection and quantification of DOI. In the HPLC, LC-10AT (Shimadzu), and Luna 5u C18 column (Phenomenex, column length 150 mm, column diameter 4.6 mm) were used, 20% methanol was used as an eluent, and the ultraviolet absorption at 262 nm was measured. Amount of the oxime derivative of DOI with 0-(4-nitrobenzyl) was quantified with standard curve thereof. It should be noted that the quantification of glucose was performed with glucose assay procedure kit (Megazyme).

Figure 4A:
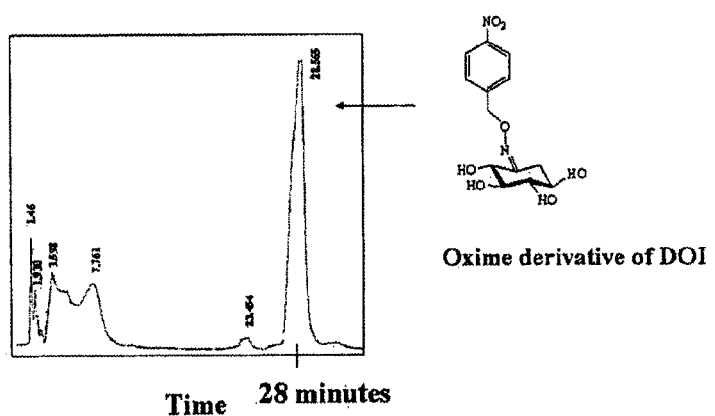
FIG. 4A is a HPLC chart showing the oxime obtained from the supernatant of the culture medium of the *E. coli* GI724Δpgi strain comprising pLEX-btrC (3 L of 2×YT, 30° C., pH 7.5, 5.5% D-glucose, 24 hours incubation).
Figure 4B:
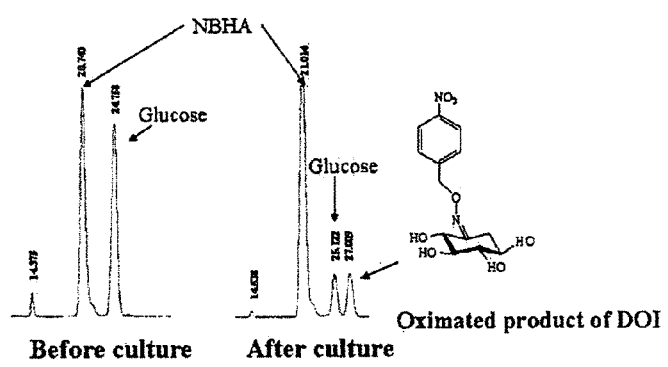
FIG. 4B is a HPLC chart showing the oxime obtained from the supernatant of the culture medium of the *E. coli* GI724Δrmf strain comprising pLEX-btrC (10 mL of 2×YT, 30° C., pH 7, 3% D-glucose, 48 hours incubation) (left chart at 0 hr culture).
Figure 6:
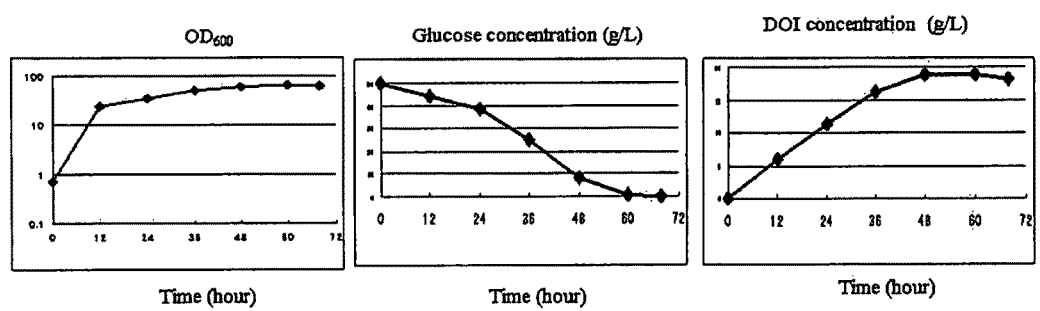
FIG. 6 is a graph showing time courses of (A) turbidity of the medium, (B) D-glucose concentration and (C) DOI production during the culture of the *E. coli* GI724ΔpgiΔzwf strain comprising pLEX-btrC (2×YT medium+3% mannitol+5% D-glucose, 3 L, 30° C., pH 7.5) (the horizontal axes correspond to the elapsed time after addition of glucose).
Figure 7:
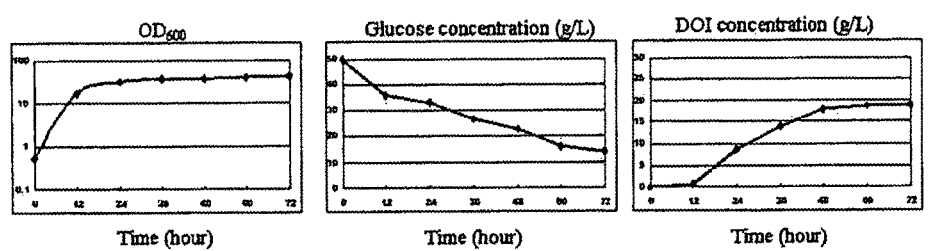
FIG. 7 is a graph showing time courses of (left) turbidity derived from microorganisms, (center) D-glucose concentration and (right) DOI production during the culture of the *E. coli* GI724ΔpgiΔzwfΔpgm strain comprising pLEX-btrC (2×YT medium+5% D-glucose+0.5% mannitol, 3 L, 30° C., pH 7) (the horizontal axes correspond to the elapsed time after addition of glucose).
Figure 8:
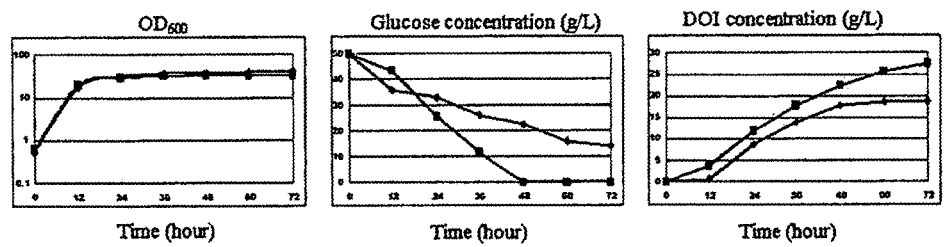
FIG. 8 is a graph showing time courses of (left) turbidity derived from microorganisms, (center) D-glucose concentration and (right) DOI production during the culture of the *E. coli* GI724ΔpgiΔzwfΔpgm strain (♦) comprising pLEX-btrC, and the *E. coli* GI724ΔpgiΔzwfΔpgm strain (■) comprising pGAP-btrC/pGAD-btrC (2×YT medium+5% D-glucose+0.5% mannitol, 3 L, 25° C., pH 6-7) (the horizontal axes correspond to the elapsed time after addition of glucose).
Figure 9:
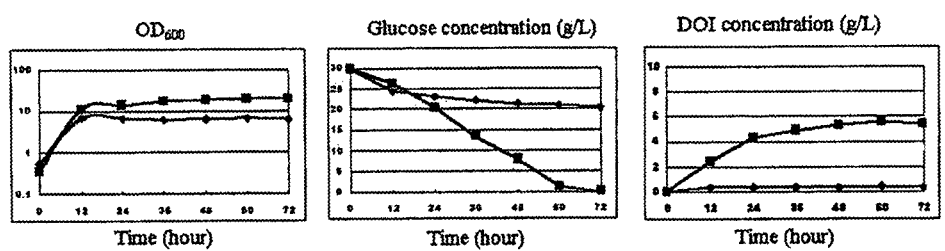
FIG. 9 is a graph showing time courses of (left) turbidity derived from microorganisms, (center) D-glucose concentration in the medium and (right) DOI production during the culture of the wild type *E. coli* (♦) comprising pLEX-btrC, and the *E. coli* GI724Δrmf strain (■) comprising pLEX-btrC (2×YT medium+3% D-glucose, 10 mL, 30° C., pH 7) (the horizontal axes correspond to the elapsed time after addition of glucose).

As shown in FIGS. 4A and 4B, the peak corresponding to the oxime derivative of DOI was confirmed in the HPLC analysis. In addition, FIGS. 5 to 7 show a time course of the DOI production, turbidity of the medium and the D-glucose concentration.

Reference Example 1

Synthesis of DOI Using the GI724Δpgi Strain Comprising pLEX-btrC>

The GI724Δpgi strain comprising pLEX-btrC was inoculated in 35 mL of a preculture solution contained in 300 mL conical flask (RMG medium: 0.6% sodium hydrogen phosphate, 0.3% potassium dihydrogen phosphate, 0.05% sodium chloride, 0.1% ammonium chloride, 2% casamino acid, 1% glycerin, 1 mM magnesium chloride), and cultured for 15 hours. Next, 1% of the strain of the preculture solution was inoculated in 3 L of 2×YT medium contained in 10 L of jarfermenter. The strain was cultured in a condition of 30° C. of culture temperature, 300 rpm of mixing speed, 10 L air per minute and pH 7.7 until O.D. 600 nm was reached to 0.7, and then 2% or 5% of D-glucose was added in the culture, and the culture was further cultured for 24 hours. The culture solution at the indicated time points was centrifuged to remove the strain, thereby collecting a culture supernatant 11.

Reference Example 2

Synthesis of DOI Using the GI724ΔpgiΔzwfΔpgm Strain Comprising pLEX-btrC>

The GI724ΔpgiΔzwfΔpgm strain comprising pLEX-btrC was inoculated in 50 mL of a preculture solution contained in 300 mL conical flask (0.6% disodium hydrogen phosphate, 0.3% potassium dihydrogen phosphate, 0.05% sodium chloride, 0.1% ammonium chloride, 2% casamino acid, 1% glycerol, 1 mM magnesium chloride), and cultured for 15 hours. Next, 1% of the strain of the preculture solution was inoculated in 3 L of 2×YT medium contained in 10 L of jarfermenter (MDL-6C, made by Marubishi Bioengineering). The strain was cultured in a condition of 25° C. of culture temperature, 300 rpm of mixing speed, 10 L air per minute and pH 7.0 until O.D. 600 nm was reached to 0.7, and then 5% of D-glucose was added in the culture, and the culture was further cultured for 72 hours. The culture solutions before and after the addition of D-glucose were collected, and were centrifuged to remove the strain, thereby collecting culture supernatants 12 and 13.

Reference Example 3

Synthesis of DOI Using the Wild Type GI724 Strain Comprising pLEX-btrC>

The wild type GI724 strain comprising pLEX-btrC was inoculated in 3 mL of a preculture solution contained in test tube (0.6% disodium hydrogen phosphate, 0.3% potassium dihydrogen phosphate, 0.05% sodium chloride, 0.1% ammonium chloride, 2% casamino acid, 1% glycerol, 1 mM magnesium chloride), and cultured for 15 hours. 1% of the strain of the preculture solution was inoculated in 10 mL of 2×YT medium contained in L-shaped test tube. The strain was cultured in a condition of 30° C. of culture temperature, 160 rpm of mixing speed and pH 7.0 until O.D. 600 nm was reached to 0.7, and then 3% of D-glucose was added in the culture, and the culture was further cultured for 72 hours. The culture solutions at the indicated time points were collected, and were centrifuged to remove the strain, thereby collecting a culture supernatant 14.

Reference Example 4

Measurement of DOI Production

Quantification of the DOI production accumulated in the culture supernatants 11 to 14 as obtained was performed as follows.

One volume of water, two volumes of methanol and 15 mg/ml of O-(4-nitrobenzyl)hydroxylamine (NBHA), with regard to the volume of the culture supernatant 11 were added and mixed in the culture supernatant 11, and incubated at 60° C. for 1 hour to obtain the oxime derivative of DOI.

With regard to the culture supernatants 12, 13 and 14, 9 volumes of distilled water was added to the supernatant(s), and added one volume of methanol with regard to this solution, and then 30 mg/ml of O-(4-nitrobenzyl)hydroxylamine hydrochloride salt (NBHA) was added and mixed, and incubated at 60° C. for 1 hour to obtain the oxime derivative of DOI.

The solvent was evaporated from the solution of the oxime derivative of DOI so obtained with Speed Vac System (ISS110, made by Thermo), the obtained oxime derivative of DOI was dissolved in an appropriate volume of methanol, the aliquot was analyzed with HPLC (high-performance liquid chromatography) to perform the detection and determination of the amount of DOI. In the HPLC, LC-9A (Shimadzu), and Luna 5u C18 column (Phenomenex, column length 150 mm, column diameter 4.6 mm) were used, 20% methanol was used as an eluent, and the ultraviolet absorption at 262 nm was measured. Amount of the oxime derivative of DOI with 0-(4-nitrobenzyl) was quantified with Standard curve thereof.

Example 8

A Method Using a Mixed Bed Column of Amberlite IR120 and Amberlite IRA410>

Figure 10:
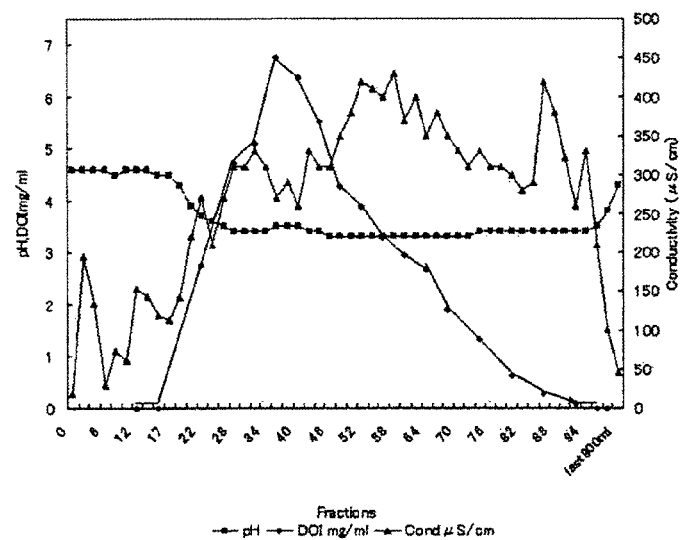
FIG. 10 is a graph of pH, conductivity and DOI concentration at each fraction obtained from the eluent wherein the cultured medium is passed through the ion exchange resin to obtain the eluent, in accordance with Example 8.
Figure 11:
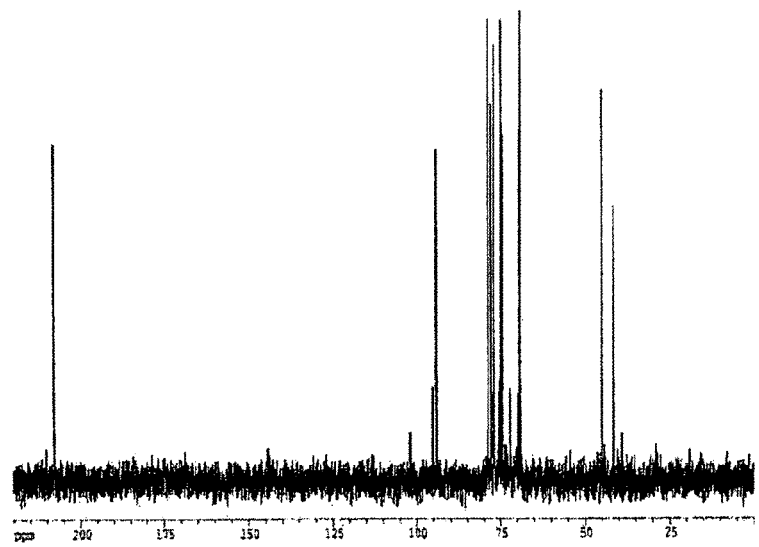
FIG. 11 is $^{13}$C-NMR spectrum of DOI as purified and obtained in accordance with the method of Example 8.

200 mL of a hydrogen form of Amberlite IR 120 and 200 mL of an acetate form of Amberlite IRA410 were mixed, and filled in a column ($\phi$5 cm×25 cm). 100 mL of the culture medium as obtained from the reference example 1 and adjusted to pH 2.96 (containing 1.4 g of DOI) was applied to the column, an elution was performed with water at 2 mL per minute. 6 mL of eluate per a fraction was collected and pH and the conductivity of every other fraction were measured. In addition, the quantity of DOI was measured at every three fractions. The quantity measurement of DOI was performed such that DOI was derivatized into the O-(4-nitrobenzyl) oxime and then the peak area on the HPLC was measured, and the quantity of DOI was estimated from the calibration curve based on the peak area. The result so obtained is shown in FIG. 10. In addition, after the fractions were grouped into 4 blocks and each block was freeze-dried, the purity and amount of DOI on each group was measured. The result is shown in Table 2. $^{13}$C-NMR spectrum of the purified DOI so obtained is shown in FIG. 11. The $^{13}$C-NMR spectrum was measured with DPX-250 NMR apparatus ($^{13}$C nucleus was resonated at 67.5 MHz) made by Bruker with regard to the sample dissolved in deuterated water.

Example 9

A Method Using a Mixed Bed Column of Amberlite IR200 and Amberlite IRA410>

Figure 12:
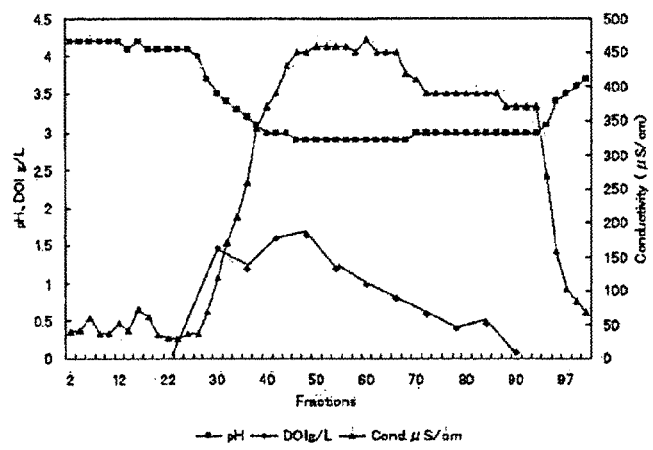
FIG. 12 is a graph of pH, conductivity and DOI concentration at each fraction obtained from the eluent wherein the cultured medium is passed through the ion exchange resin to obtain the eluent, in accordance with Example 9.
Figure 13:
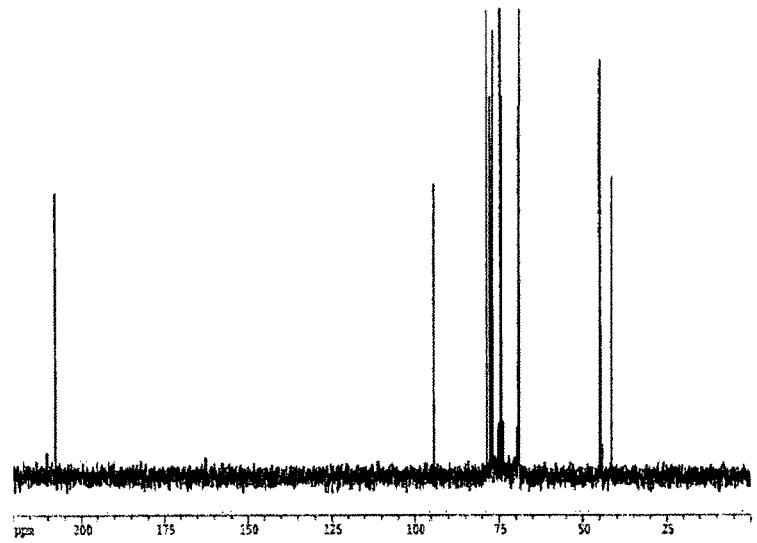
FIG. 13 is $^{13}$C-NMR spectrum of DOI as purified and obtained, in accordance with the method of Example 9.

200 mL of a hydrogen form of Amberlite IR 200 and 200 mL of an acetate form of Amberlite IRA410 were mixed, and filled in a column ($\phi$5 cm×25 cm). 100 mL of the culture medium as obtained from the reference example 1 adjusted to pH 2.97 (containing 562 mg of DOI) was applied to the column, an elution was performed with water at a flow rate of 2 mL per minute. 6 mL of eluate per a fraction was collected and pH and the conductivity of every other fraction were measured. In addition, the quantitative of DOI was performed at every three fractions. The result so obtained is shown in FIG. 12. In addition, after the fractions were grouped into 4 blocks and each block was freeze-dried, the purity and amount of DOI on each group were measured. The result is shown in Table 3. $^{13}$C-NMR spectrum of the purified DOI so obtained is shown in FIG. 13. The measurement of quantity of DOI and measurement of the $^{13}$C-NMR spectrum were performed in accordance with Example 8

TABLE 2

|  | weight (mg) | amounts of DOI (mg) | purity (%) |
|---|---|---|---|
| Fr. 27-47 | 207 | 42 | 20.3 |
| Fr. 48-60 | 252.4 | 226.3 | 89.7 |
| Fr. 61-95 | 253.9 | 117.8 | 46.4 |
| Fr. 96- | 24.6 | 13.2 | 53.5 |
| Total | 737.9 | 399.3 | 54.1 |

TABLE 3

|  | weight (mg) | amounts of DOI (mg) | purity (%) |
|---|---|---|---|
| Fr. 26-45 | 85.7 | 71.4 | 83.8 |
| Fr. 46-71 | 120 | 114.1 | 95.1 |
| Fr. 72-95 | 31.6 | 25.1 | 79.5 |
| Fr. 96- | 11.9 | 1.3 | 10.8 |
| Total | 249.2 | 211.9 | 85.0 |

Example 10

A Method Using a Double Bed Column of Amberlite 200CT and Amberlite IRA96SB>

Figure 15:
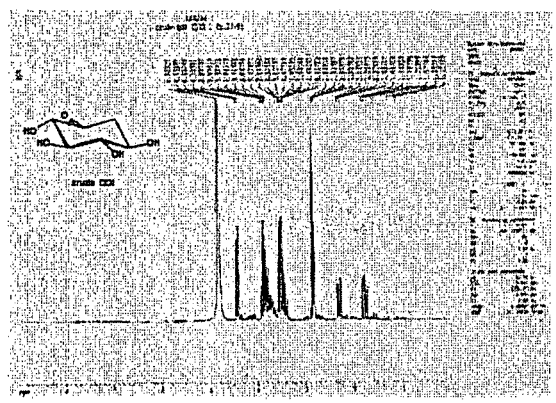
FIG. 15 is $^{1}$H-NMR spectrum of DOI as purified and obtained, in accordance with the method of Example 10.

A DOI containing culture solution (DOI amount: 22.1 g/850 mL) was applied on a cation exchange resin column (Amberlite 200CT, a hydrogen form, 400 mL) and eluted with water. Fractions which contain DOI in the obtained eluents analyzed by TLC were applied on an anion exchange resin column (Amberlite IRA96SB, an acetate form, 600 mL), and eluted with water. Fractions which contain DOI in the obtained eluents confirmed by the analysis with TLC were concentrated in vacuo. As the result, 20.8 g of DOI which has a purity as observed in a $^1$H-NMR spectrum shown in FIG. 15 was obtained. The purity is approximately same as those obtained from the method of the purification using the above-mentioned mixed bed column. The $^1$H-NMR spectrum was measured with DPX-250 NMR apparatus made by Bruker with regard to the sample dissolved in deuterated water.

Example 11

Figure 16:
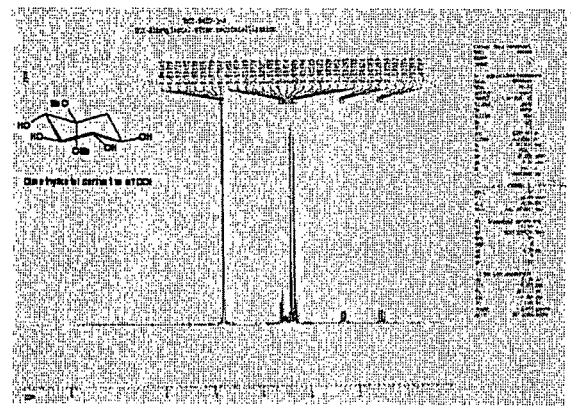
FIG. 16 is $^{1}$H-NMR spectrum of DOI as purified and obtained, in accordance with the method of Example 11.

A Method for Restoring 2-Deoxy-Scyllo-Inosose, Following to Convert DOI into the Dimethylketal Derivative, to Crystallize and to Purify The purified DOI as obtained in Example 10 was dissolved in methanol (835 mL) and trimethoxymethane (310 mL) and p-toluenesulfonic acid monohydrate (2.12 g) were added, and stirred for 3 hours. Then, the reaction mixture was neutralized with sodium bicarbonate (30.6 g), and the vacuum concentration was performed after filtration. The residue was dissolved in methanol, three volumes of silica gel (C-200, 60 g) were added, and the vacuum concentration was performed to adsorb DOI onto the surface of the silica gel. The DOI adsorbed onto the silica gel was filled in a silica gel column with ethyl acetate and methanol (5:1). Then, DOI was eluted from the column with mixed solvent of ethyl acetate and methanol (5:1). The eluents which contain DOI were collected and the vacuum concentration was performed with the collected eluents, thereby obtaining the dimethylketal derivative of DOI (20.7 g). Subsequently, a solution of the dimethylketal derivative dissolved in 25 mL of methanol was added to 100 mL of chloroform and 7.5 mL of hexane under heating, and then cooled to precipitate and separate white crystals, thereby obtaining the crystal of 2-deoxy-scyllo-inosose dimethylketal (9.1 g). Any signals originated from any impurities were not observed in $^1$H-NMR as shown in FIG. 16.

Figure 17:
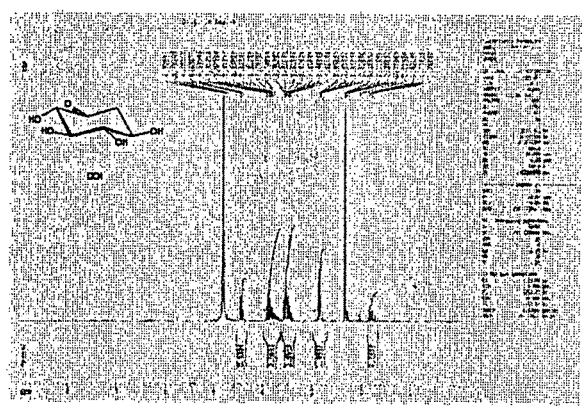
FIG. 17 is $^{1}$H-NMR spectrum of DOI as purified and obtained, in accordance with the method of Example 12.

The crystals of the dimethylketal derivative (995 mg) were dissolved in acetone (22 mL), and p-toluenesulfonic acid monohydrate (280 mg) and distilled water (6 mL) were added, and the solution was stirred for 5 hours. After the starting materials were disappeared by confirming with TLC analysis, the vacuum concentration was performed. The residue dissolved in water was applied on an anion exchange resin column (IRA96SB, an acetate form, 10 mL), and the eluents containing the target product were concentrated to quantitatively obtain highly purified DOI (770 mg). Any signals originated from any impurities were not observed in $^1$H-NMR as shown in FIG. 17.

[Statement of Microorganism as Deposited]

Statements of microorganism as deposited which is used in the present invention are as follows.

*Escherichia coli*
GI724ΔpgiΔzwfΔpgm/pGAP-btrC/pGAD-btrC
FERM AP-20809
 1. Name of organization of receipt: National Institute of Advanced Industrial Science and Technology/International Patent Organism Depositary
 2. Receiving date: Feb. 24, 2006
 3. Number of receipt: FERM AP-20809

*Escherichia coli*
GI724ΔrmfΔpgi/pLEX-btrC
FERM AP-20808
 1. Name of organization of receipt: National Institute of Advanced Industrial Science and Technology/International Patent Organism Depositary
 2. Receiving date: Feb. 24, 2006
 3. Number of receipt: FERM AP-20808

INDUSTRIALLY APPLICABILITY

According to the present invention, it is possible to manufacture DOI with high purity which is a starting material for manufacturing various types of six-membered carbocyclic compounds, by fermentation using biomass-derived starting materials such as starch which are regenerative resources, instead of chemical compounds derived from petroleum in the prior art.

As mentioned above, the present invention has been described in accordance with the preferred embodiments thereof. It is obvious that modifications and alterations can be made to the embodiments, without departing from the spirit and scope of the present invention as defined in the Claims, although the present invention has been described in accordance with the specific embodiments. That is, the present invention shall not be construed in limiting into the detail of the embodiments and the drawing as attached.

What is claimed is:

1. An isolated host cell comprising a gene expression cassette having a gene encoding 2-deoxy-scyllo-inosose synthase with at least one disrupted gene selected from the group consisting of pgi gene encoding phosphoglucose isomerase, zwf gene encoding glucose-6-phosphate 1-dehydrogenase, pgm gene encoding phosphoglucomutase, and rmf gene encoding ribosome modulation factor involved in modification of protein synthesis during stationary phase, and wherein the host cell is *Escherichia coli*, and 2-deoxy-scyllo-inosose is synthesized within the host cell.

* * * * *